US008535644B2

(12) United States Patent
Haghgooie et al.

(10) Patent No.: US 8,535,644 B2
(45) Date of Patent: Sep. 17, 2013

(54) TUNABLE HYDROGEL MICROPARTICLES

(75) Inventors: Ramin Haghgooie, Arlington, MA (US); Patrick Seamus Doyle, Cambridge, MA (US); Mehmet Toner, Wellesley, MA (US); Daniel Colin Pregibon, Cambridge, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 705 days.

(21) Appl. No.: 12/578,303

(22) Filed: Oct. 13, 2009

(65) Prior Publication Data
US 2010/0092393 A1    Apr. 15, 2010

Related U.S. Application Data

(60) Provisional application No. 61/195,844, filed on Oct. 10, 2008.

(51) Int. Cl.
*A61K 9/50* (2006.01)
*A61K 49/00* (2006.01)
*C08J 3/28* (2006.01)
*C09K 11/02* (2006.01)
*C09D 7/00* (2006.01)

(52) U.S. Cl.
USPC ............... 424/9.6; 424/501; 522/153; 522/6; 428/402

(58) Field of Classification Search
None
See application file for complete search history.

(56) References Cited

U.S. PATENT DOCUMENTS

| | | | |
|---|---|---|---|
| 5,808,103 A | 9/1998 | Ward et al. | |
| 6,488,872 B1 | 12/2002 | Beebe et al. | |
| 6,911,227 B2 | 6/2005 | Hubbell et al. | |
| 2004/0014901 A1 | 1/2004 | Heide et al. | |
| 2005/0043428 A1 | 2/2005 | Caneba et al. | |
| 2006/0054506 A1 | 3/2006 | Natan et al. | |
| 2006/0228386 A1 | 10/2006 | Stephens et al. | |
| 2007/0054119 A1 | 3/2007 | Garstecki et al. | |
| 2007/0105972 A1 | 5/2007 | Doyle et al. | |
| 2007/0126982 A1 | 6/2007 | Myung et al. | |
| 2010/0028994 A1* | 2/2010 | DeSimone et al. | 435/325 |

FOREIGN PATENT DOCUMENTS
WO   WO 2007024323 A2 *  3/2007

OTHER PUBLICATIONS

Datta, A., "Characterization of Polyethylene Glycol Hydrogels for Biomedical Applications", 2007, pp. 1-107.*
Riley, S.OL., et al., "Formulation of PEG-based hydrogels affects tissue-engineered cartilage construct characteristics", 2001, J. Mater. Sci., 12, pp. 983-990.*
Peyton, S.R., et al., "The use of poly(ethylene glycol) hydrogels to investigate the impact of ECM chemistry and mechanics on smooth muscle cells", 2006, Biomaterials, 27, pp. 1-15.*
Scienceblog, "Discovery: Scientists find new reason red blood cells cut blood flow in sickle cell disease victims", Jun. 2001, accessed from: http://scienceblog.com/community/older/2001/E/200115267.html, pp. 1-3.*
International Search Report and Written Opinion, PCT/US09/60515, Dec. 18, 2009, pp. 1-12.
International Search Report and Written Opinion, PCT/US2009/061474, Oct. 21, 2009, pp. 1-11.
Elliott et al., "Kinetic modeling of the elect of solvent concentration on primary cyclization during polymerization of multifunctional monomers", "Chemical Engineering Science", 2001, pp. 3173-3184, vol. 56, Publisher: Elsevier Science Ltd.
Elliott et al., "Structure and swelling of poly(acrylic acid) hydrogels: effect of pH, ionic strength, and dilution on the crosslinked polymer structure", "Polymer", 2004, pp. 1503-1510, vol. 45.

* cited by examiner

*Primary Examiner* — Michael G Hartley
*Assistant Examiner* — Lance Rider
(74) *Attorney, Agent, or Firm* — Evans & Molinelli PLLC; Eugene J. Molinelli

(57) ABSTRACT

Techniques are provided to produce and use non-spherical colloidal particles with independently tuned size, shape, flexibility, and chemical properties. A pre-polymer mixture for forming hydrogel particles includes a percentage of PEGDA selected to impart a target stiffness to the particles and includes, a percentage of acrylic acid selected to impart an independent target chemical function to the particles. The mixture also includes a percentage of photo-initiator to polymerize PEGDA upon exposure to a light source to impart an independently selected target size or shape or both to the particles.

14 Claims, 16 Drawing Sheets

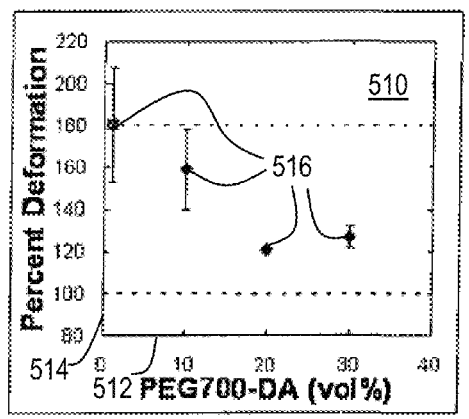
FIG. 5A
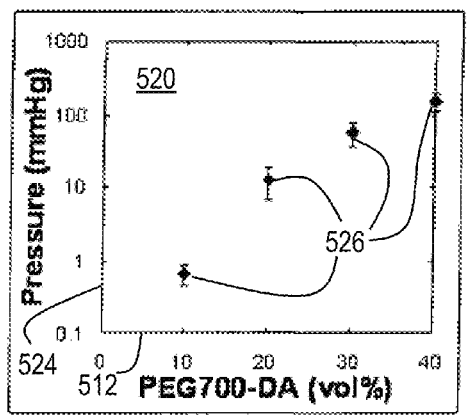
FIG. 5B
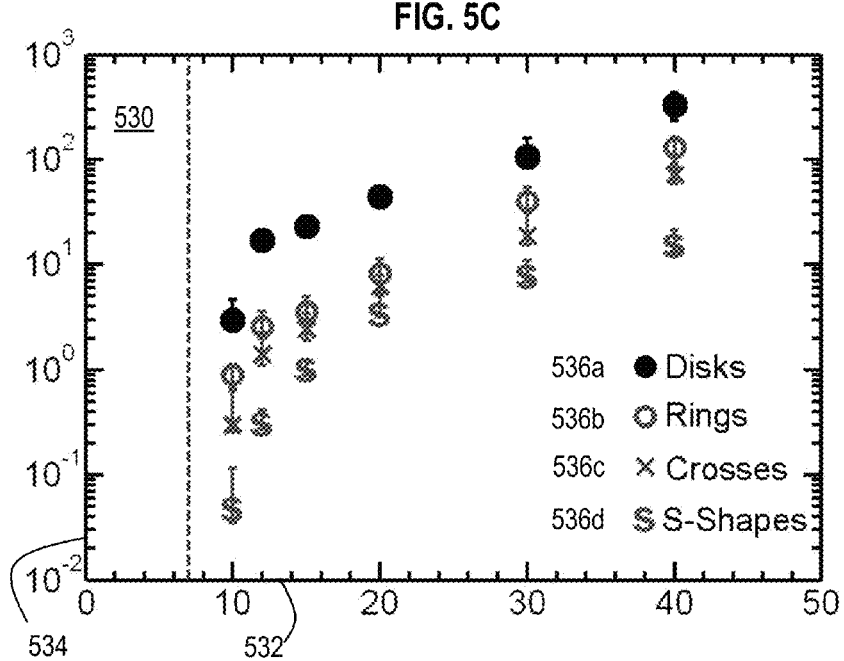

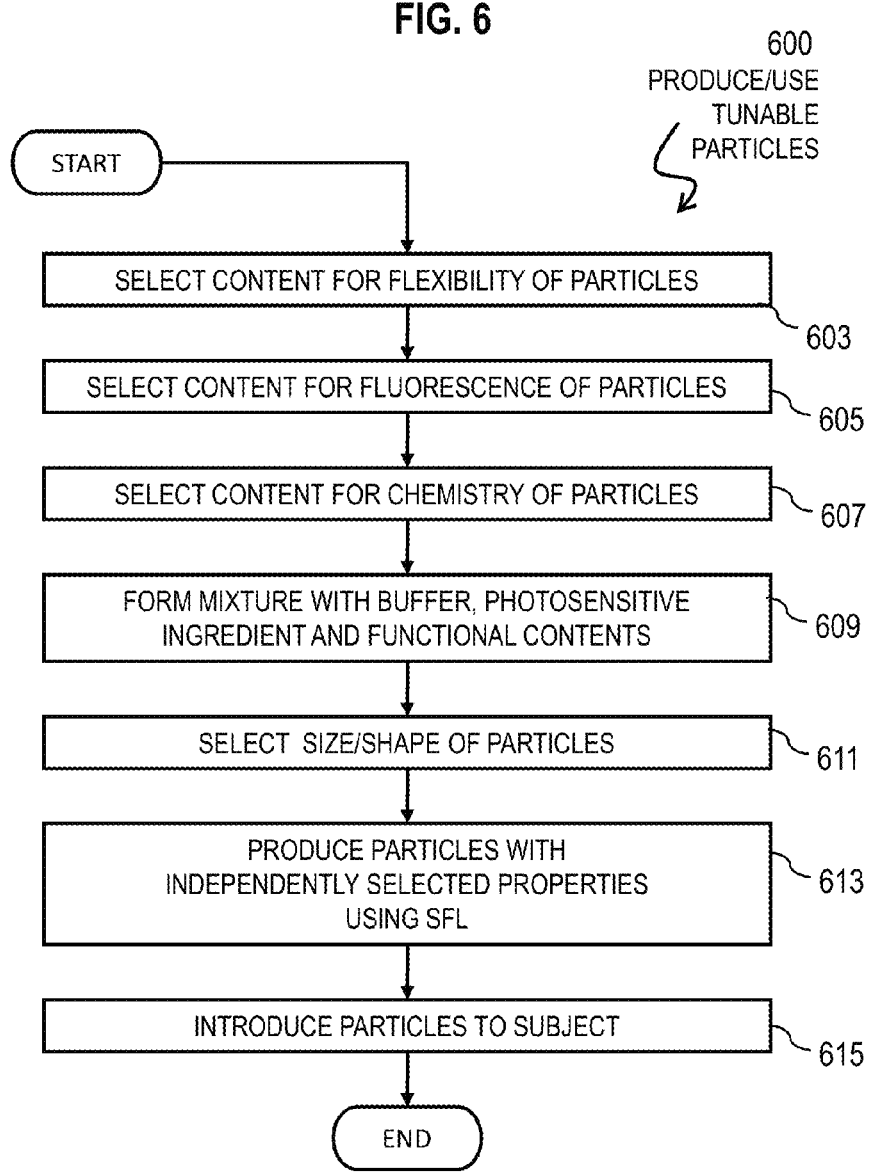

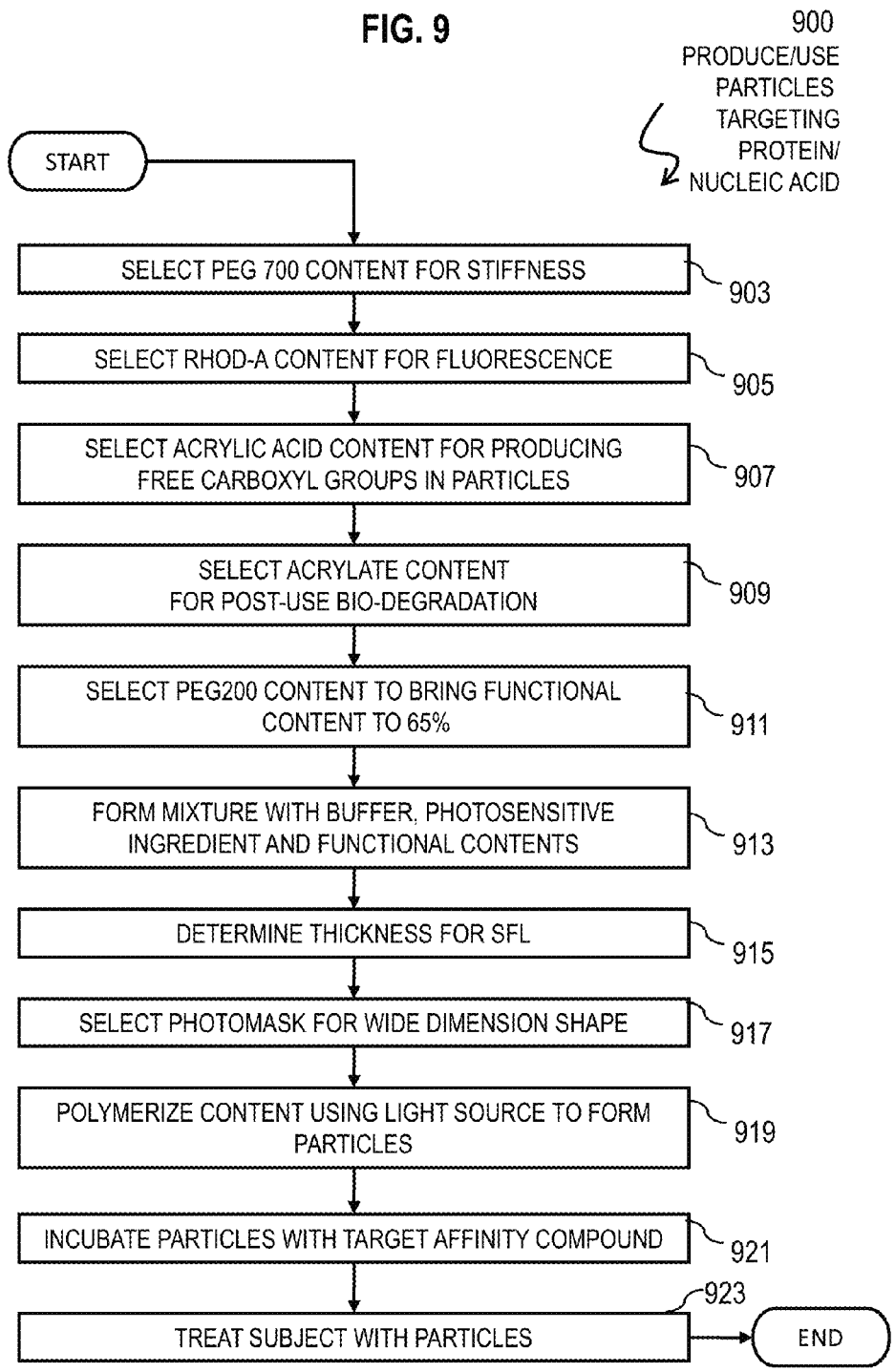

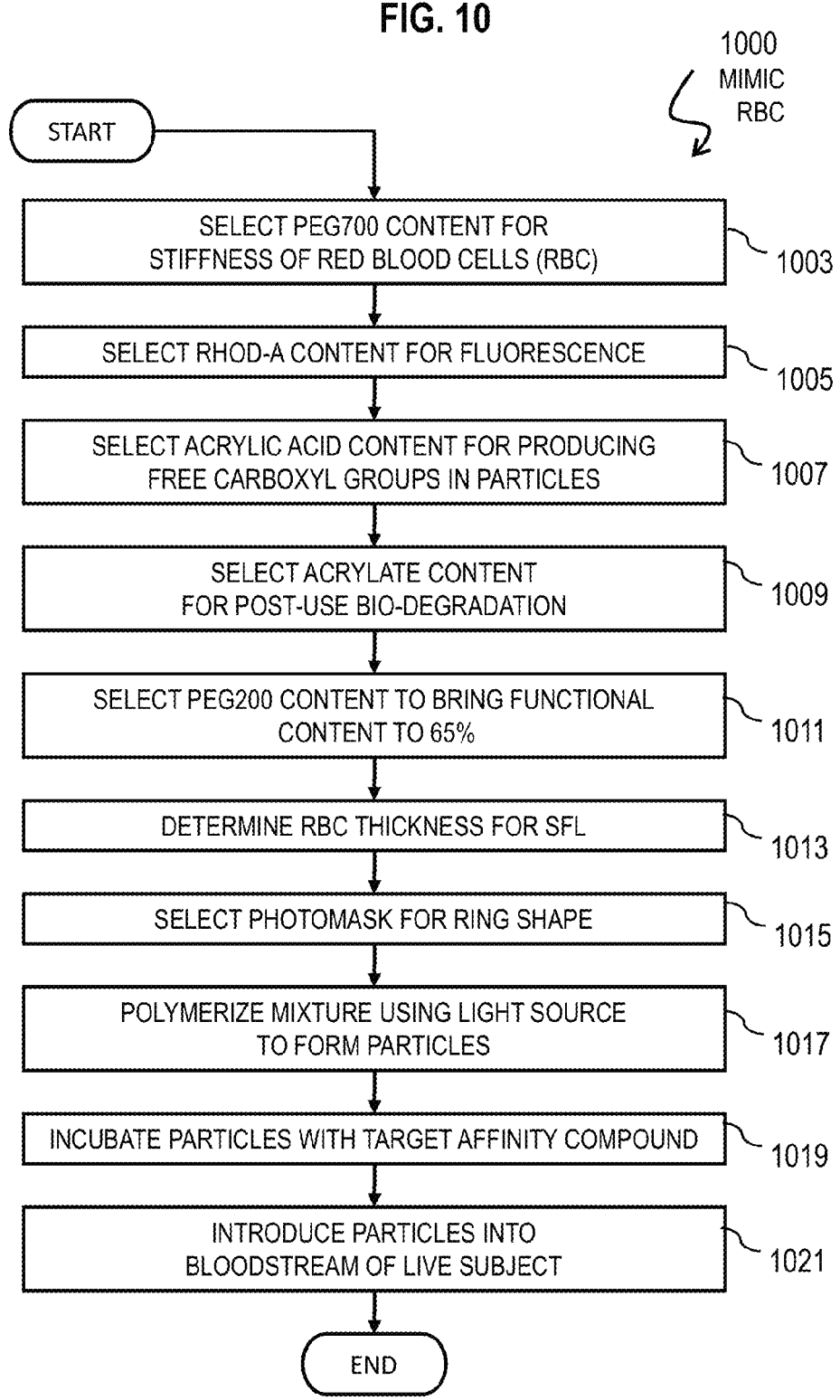

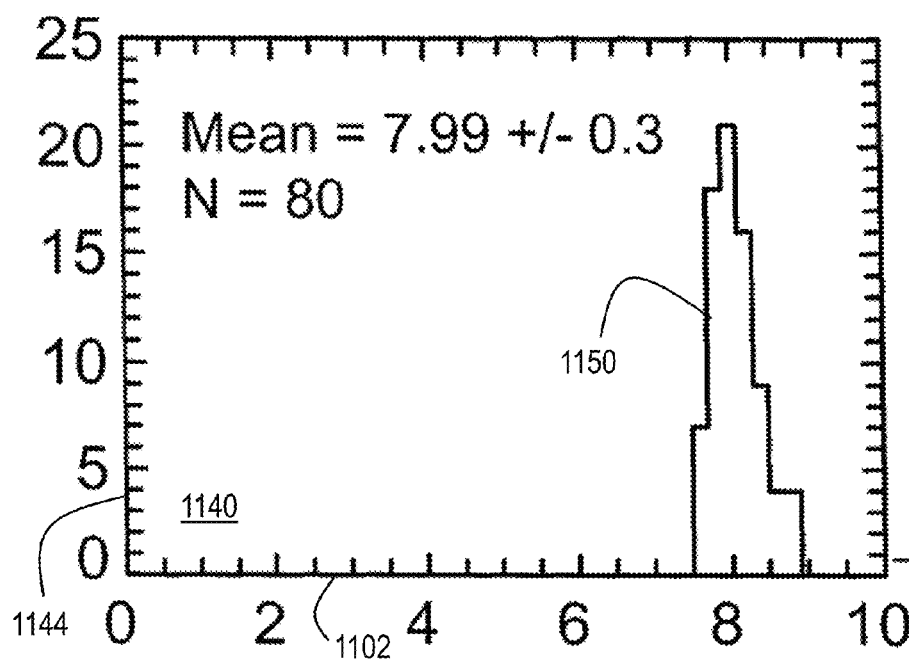
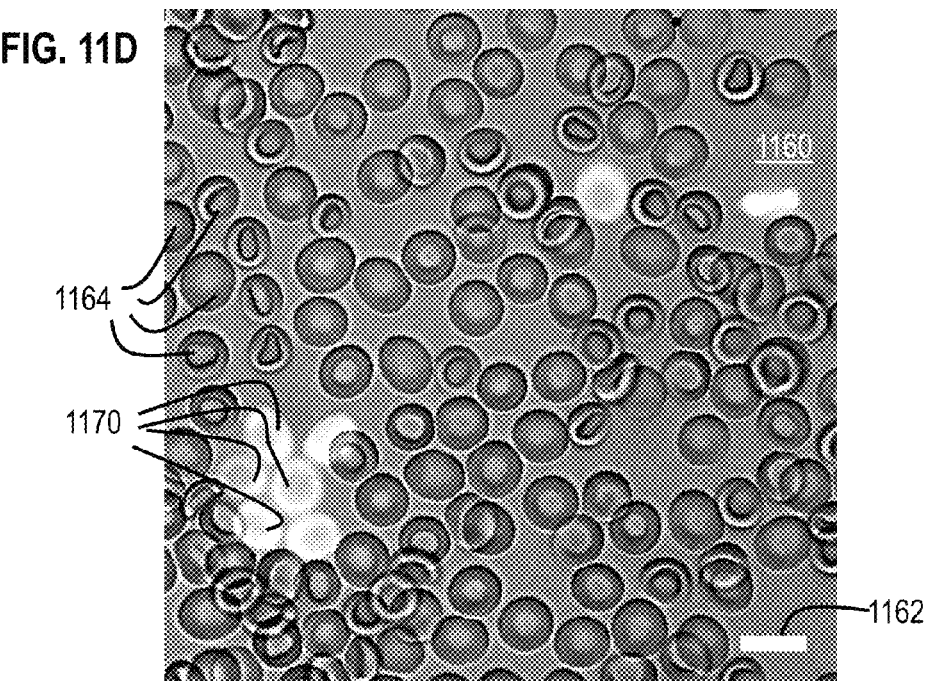

TUNABLE HYDROGEL MICROPARTICLES

CROSS-REFERENCE TO RELATED APPLICATIONS

This application claims benefit of Provisional Appln. 61/195,844, filed Oct. 10, 2008, the entire contents of which are hereby incorporated by reference as if fully set forth herein, under 35 U.S.C. §119(e).

This application is related to U.S. utility application Ser. No. 11/867,217 filed Oct. 4, 2007 and published as US Patent Application Publication US 2008/0176216 on Jul. 24, 2008 (hereinafter Doyle II), the entire contents of which are hereby incorporated by reference as if fully set forth herein.

This application is related to U.S. utility application Ser. No. 11/586,197 filed Oct. 25, 2006 and published as US Patent Application Publication US 2007/0105972 on May 10, 2007 (hereinafter Doyle II), the entire contents of which are hereby incorporated by reference as if fully set forth herein.

STATEMENT OF GOVERNMENTAL INTEREST

This invention was made with Government support under grant P41EB002503 awarded by the National Institutes of Health and grant CTS-0239012 awarded by the National Science Foundation. The Government has certain rights in the invention.

BACKGROUND

Spherical colloidal particles are ubiquitous in drug delivery, in vivo and in vitro diagnostics, as well as additives in almost every industry (food, cosmetics, paints, etc). The ability of these particles to accurately interact with biological organisms, cells and molecules in a complex mixture or in vivo is crucial in both basic research and clinical settings. The vast majority of particles used in suspension arrays are optically encoded latex microspheres with diameters between 0.3 and 10 microns (1 micron=$10^{-6}$ meters) that can be interrogated and decoded with laser-based flow cytometry (measurement of cell sized particles). Optical encoding is accomplished by swelling the spheres with fluorescent organic dyes with different emission spectra. While recent advances in the field of colloid synthesis have produced anisotropic (non-spherical) particles, the ability to independently control size/shape, chemistry, and flexibility has not been demonstrated. Current methods for altering flexibility of colloids rely upon using different materials to synthesize the particles. For instance, wax can be used to create softer colloidal particles; but wax lacks the flexible chemistry necessary for a variety of applications. There is not a single colloidal system known to the authors that brings together independent control of size/shape, chemistry, and flexibility.

EXAMPLE EMBODIMENTS

Applicants have recognized a need to independently control size/shape, chemistry, and flexibility of colloids for biological interactions. Techniques are provided to produce and use non-spherical colloidal particles with independently tuned size, shape, flexibility, and chemical properties.

In one set of embodiments, a pre-polymer mixture, for forming hydrogel particles, includes a percentage of PEGDA selected to impart a predetermined stiffness to the particles. The mixture also includes a percentage of acrylic acid selected independently to impart a capacity to bind to a target affinity molecule. The mixture also includes a percentage of photo-initiator to polymerize PEGDA upon exposure to a light source to impart an independently selected target size or shape or both to the particles.

In another set of embodiments, a particle of a particular shape includes PEGDA, an active substance and PEG. A total amount of PEG, PEGDA and active substance is between about 30 percent by volume and about 95 percent per volume of the particle.

In another set of embodiments, a method includes providing a pre-polymer mixture and exposing the pre-polymer mixture to the light source shaped by a mask having a particular shape to produce particles that exhibit the particular shape. The pre-polymer mixture includes a first fraction and a remaining fraction. The first fraction comprises PEGDA in an amount selected to impart a predetermined stiffness to a particle produced by the method, PEG, and an active substance. The remaining fraction comprises a photo-initiator to polymerize PEGDA upon exposure to a light source.

In another set of embodiments, composition comprises a particle of a particular shape. The particle comprises PEGDA, an active substance and PEG. A total amount of PEG, PEGDA and active substance is from about 30 to about 95 percent by volume of the particle.

In another set of embodiments, a ring shaped hydrogel particle has a diameter and flexibility of a red blood cell.

In another set of embodiments, a method includes providing a pre-polymer mixture, exposing the pre-polymer mixture to a light source shaped by a mask to produce particles that exhibit a ring shape having a size of a red blood cell, and administering the particles into a bloodstream of an animal. The pre-polymer mixture includes a first fraction and a remaining fraction. The first fraction comprises PEGDA in an amount selected to impart a predetermined stiffness comparable to stiffness of red blood cells to a particle produced by the method, PEG, and an active substance. The remaining fraction comprises a photo-initiator to polymerize PEGDA upon exposure to a light source.

Still other aspects, features, and advantages are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 5A is a graph that illustrates percent deformation of disk microparticles within micro-constrictions, according to various embodiments;

FIG. 5B is a graph that illustrates pressure differential to transport disk microparticles through micro-constrictions, according to various embodiments;

FIG. 5C is a graph that illustrates pressure differential to transport different shaped microparticles through micro-constrictions, according to various embodiments;

FIG. 6 is a flowchart that illustrates a method to produce and use tunable particles, according to an embodiment;

FIG. 9 is a flowchart that illustrates a method to produce and use particles targeting proteins, according to an embodiment;

FIG. 10 is a flowchart that illustrates a method to produce and use particles that mimic red blood cells, according to an embodiment;

FIG. 11A and FIG. 11B and FIG. 11C are graphs that illustrate the production of particles that mimic red blood cells, according to various embodiments;

FIG. 11D is an image that illustrates a particle among red blood cells, according to an embodiment.

DETAILED DESCRIPTION

Figure 1:
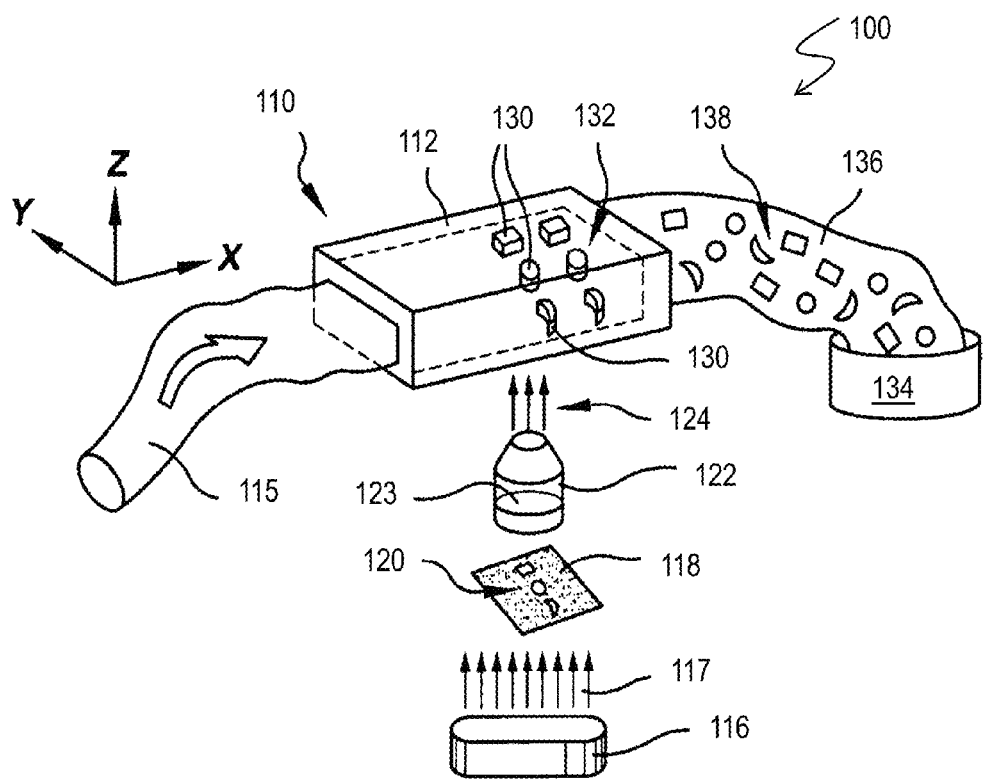
FIG. 1 is a block diagram that illustrates a system for producing tunable hydrogel microparticles, according to an embodiment.

A method and apparatus are described for producing and using tunable hydrogel particles. In the following description, for the purposes of explanation, numerous specific details are set forth in order to provide a thorough understanding. It will be apparent, however, to one skilled in the art that some embodiments may be practiced without these specific details. In other instances, well-known structures and devices are shown in block diagram form in order to avoid unnecessarily obscuring the illustrated embodiments.

Some embodiments are described below in the context of producing and using microparticles having at least one dimension no greater than 500 micrometers (μm, also called microns, 1 μm=$10^{-6}$ meters) for drug delivery in a bloodstream. However, the invention is not limited to this context. In other embodiments, the apparatus, particles, or method, or some combination, are used to detect or quantify or deliver substances to targets or add properties to articles of manufacture such as paints, cosmetics, food and medicine. As used herein targets may include biological entities such as proteins, nucleic acids, cytokines, lipids, organelles, whole cells, enzymes, antibodies, pathogens such as bacteria, viruses and toxins including those that could be used as bioterror threats, or any range of chemicals from polymers to small molecules. As used in the figures "subject" includes an animal subject, preferably a human, a biological sample, an article of manufacture (contacted with the particles).

In various embodiments, detection and quantification are based on fluorescence, chemiluminescence, magnetic properties, radioactivity, radio frequency, electrical resistance, opacity, or colorimetry, among other means. For optical approaches, single or multiple wavelengths may be used. In addition, multiple detectors or excitation sources may be used.

Drugs refer to any substance introduced for delivery to the target or that binds to a target, including any therapeutic agent such as chemotherapy agents, radioactive elements, and mechanical objects. Active substances include drugs, detection labels including fluorophores, acrylic acid (AA) and other acrylate chemistries such as acrylate monomers used to form acrylate polymers including acrylic acid, butyl acrylate, 2-ethylhexyl acrylate, methyl acrylate, ethyl acrylate, acrylonitrile, methyl methacrylate, and TMPTA methacrylate.

Some specific applications include drug discovery, drug delivery, biomarker discovery, target segregation or filtering, expression profiling, combinatorial chemistry, clinical diagnostics, or monitoring environmental samples for microorganisms or chemical agents, or introducing properties to articles of manufacture such as paints, cosmetics, foods and medicines.

As used herein a microparticle is a particle with at least one dimension in a range from about 0.1 micrometers (μm, also called microns, 1 μm=$10^{-6}$ meters) to about 500 microns. The dimensions of a particle size are characterized by a length greater than a width greater than a thickness.

Colloids are ubiquitous in industrial processes and products, pharmaceuticals, and the medical field. Until now, the colloids used in these fields have been spherical and their mechanical properties have been completely tied to the materials used to synthesize them. For instance, polystyrene colloids are the gold standard for biomedical research where the colloids can be functionalized with bio-molecules and used to assay for specific cells in a cellular sample. Polystyrene however, is a material with only a single stiffness (it is not possible to create "hard" or "soft" polystyrene colloids) and the commercially available colloids are only spherical, limiting their utility in a number of ways. Spheres by definition are the lowest surface area object for a given volume and rigid spheres only contact planar surfaces (or other spheres) at a single contact point. This is the poorest possible design for binding to cells (one of the major uses of polystyrene spheres) since the binding relies on high surface area contact.

The size and shape of microparticles strongly influences their uptake by macrophage cells. A particularly interesting length scale for polymeric particles is the cellular length scale. However, an important feature of cells and other cell-sized biological entities is their flexibility. Among the more interesting, and well studied cell types is the red blood cell (RBC), especially the human red blood cell. RBCs possess the ability to deform and squeeze through small contractions (capillaries) during circulation through the vascular system. One application is to create synthetic particles with similar attributes to RBCs for diagnosis or treatment of conditions in an organism, such as in the human body. Currently, a method does not exist for creating RBC shaped particles with tunable flexibility. Furthermore, the utility of such particles is in part due to the chemical properties of the particle that permit it to interact or not interact with cells and entities encountered in the bloodstream. Currently, a method does not exist for creating RBC sized particles with independently tunable flexibility and chemical properties. In other applications, particles with independently tunable size, shape, flexibility and chemical properties also are desirable.

With the embodiments described below, disk shaped colloids can be manufactured with a much higher surface area than spheres. Furthermore, the disks can be made very mechanically flexible so that they can bend when they come into contact with a potential binding surface, thus increasing the surface area for contact. A preferred shape is and flexibility is that of the red blood cell. Particles of other shapes and tunable flexibility can also be manufactured. Additionally, the chemistry for functionalizing the disks can be made identical to that of the polystyrene spheres or for many other applications.

A hydrogel (also called aquagel) is a network of polymer chains that are water-insoluble. A polymer is a large molecule (macromolecule) composed of repeating structural units (called monomers) typically connected by covalent chemical bonds. Hydrogels are highly absorbent (they can contain over 99% water) and possess a degree of flexibility due to their significant water content.

FIG. 1 is a block diagram that illustrates a system 100 for producing tunable hydrogel microparticles, according to an embodiment. Using the technique of stop flow lithography (SFL), as described in Doyle II, a pre-polymer mixture 115 including one or more types of monomers and a photo-initiation ingredient that promotes polymerization upon exposure to light is input to the apparatus. SFL consists of three steps in which the flow of a pre-polymer mixture, such as a liquid phase oligomer solution, is stopped, exposed to light through a photo-mask, and then restarted to flush out the polymerized particles. According to some embodiments, the pre-polymer mixture 115 includes ingredients that impart independently selected flexibility or chemical properties or detectability, or some combination, to the resultant particles 130.

The system 100 includes a microfluidic device 112 having a selected hollow cross-sectional geometry with at least one dimension less than 500 μm. The example microfluidic device 112 exhibits a rectangular cross section but a wide range of other cross section geometries can be employed in other embodiments. In one example embodiment, the microfluidic device channel width is characterized by an inner channel width of, e.g., between about 100 nanometers (m, 1 nm=$10^{-9}$ meters) and about 1 millimeter (m, 1 mm=$10^{-3}$ meters), with channel walls having a thickness of, e.g., between about 100 μm and 10 mm, and with a channel length of, e.g., between about 1 mm and 100 mm. The microfluidic device is configured to accept a stream of a pre-polymer mixture 115 that is directed to the hollow cross section, or channel, of the microfluidic device for passage through the device. The microfluidic device is formed of any suitable material. In the example arrangement of FIG. 1 the microfluidic device is constructed of, e.g., polydimethylsiloxane (PDMS) or other suitable material.

The pre-polymer mixture 115 can include a range of constituents, as explained in detail below. In an illustrated embodiment, at least one of the constituents is provided as a liquid-phase monomer that can be polymerized by a selected polymerization process, e.g., photo-polymerization, thermal polymerization, or other process. In the example system of FIG. 1 the pre-polymer mixture includes a photo-polymerizable monomer and a photosensitive initiator species (called a photo-initialization ingredient). One example of a suitable photo-polymerizable monomer is poly(ethylene glycol) diacrylate (PEG-DA), having a molecular weight in a range between about 50 and about 10000 (called PEGDA herein), with 2-hydroxy-2-methyl-1-phenyl-propan-1-one employed as the photosensitive initiator species. The monomer stream can also include other selected monomers such as PEG, as well as particles, molecules, porogens, and other species. The monomer stream advantageously includes one or more liquid-phase components that enable passage of the stream through the microfluidic device 112

At one or more points along the microfluidic device is provided stimulation for enabling the formation and polymerization of particles in the monomer stream. For the example of FIG. 1 in which the monomer stream includes a photo-polymerizable monomer PEGDA, at one or more selected points along the length of the microfluidic device there is provided a source 116 of illumination 117 that is directed toward the microfluidic device 112. The walls of the microfluidic device are preferably substantially transparent to the wavelength of the illumination 117. Visible light, ultraviolet (UV) light, infrared (IR) light, or other wavelength of light can be employed as suited for a selected monomer species. For the PEGDA, UV illumination is a suitable polymerizing radiation.

The polymerizing radiation is shaped in correspondence with desired particle shapes. For example, interposed between the illumination source and the microfluidic device is provided one or more lithographic masks or other lithographic system for shaping the illumination. In the example of FIG. 1, there is provided a dark field lithographic mask 118 including one or more shapes 120 desired for particles to be synthesized. As shown in FIG. 1 the mask can include a plurality of distinct shapes or can include a number of replications of a single shape.

In the illustrated embodiment, a lens system 122 is interposed between the lithographic mask and the microfluidic device if desired for controlling magnification, focus, or other aspect of the illumination 117 directed through the mask. The illumination exits the lens system and is directed to the microfluidic device. In accordance with various embodiments, the illumination is temporally controlled to provide pulses of illumination of a selected duration. A shutter 123 or other mechanism for controlling the duration of illumination is advantageously provided in a suitable configuration with the lens system 122 and illumination source 116. The duration of each illumination pulse is set based on the flow rate of the stream, the polymerizing characteristics of the monomers in the stream, and the desired shape of a particle. The flow rate of the monomer stream is also controlled, and can be stopped, in coordination with the temporal control of the illumination. The illumination pulses can be provided as a sequence of pulses, each of a selected duration, or as a single long-duration pulse, as prescribed for a given application.

Exposing microfluidic device 112 to a pulse of the shaped illumination 124 polymerizes mask-defined shaped microstructure particles 130 (also called microstructures or polymerized microstructures or polymerized particles or hydrogel particles) directly in the stream of the pre-polymer mixture.

The illumination exposure simultaneously defines the shapes of polymeric particles and polymerizes the shaped particles. This dual lithography-polymerization action occurs in the continuous phase of the stream; that is, the one or more liquid-phase constituents in the stream operate as a continuous phase of the stream and are themselves polymerized in some embodiments. Thus the polymerized particles resulting from the dual lithography-polymerization action include polymeric material from the continuous phase of the monomer stream in such embodiments.

As stated above, flow of the stream can be controlled in a coordinated manner with the illumination exposure to, in turn, control characteristics of the polymerization. The flow rate and exposure duration are preferably together selected such that there is sufficient dwell time of a given volume of the monomer stream at the site of illumination exposure for substantially full polymerization of mask-defined shaped particles in the stream. If desired, the stream flow can be substantially stopped in coordination with illumination pulse exposure. With continuous monomer stream flow, a high synthesis through-put, e.g., 100 particles per second and greater, can be achieved. Such can further be enhanced with the inclusion of multiple illumination points along the length of the microfluidic device, in the manner described above, and by increasing the illumination area and the corresponding number of microstructure shapes projected to the increased area.

Once particles 130 are polymerized in the stream, the particles 130 advect through un-polymerized monomer stream or other liquid phase through the microfluidic device. A set 132 of such particles are schematically shown in FIG. 1 downstream of the lithography-polymerization point. The volume of un-polymerized liquid phase constituents remaining in the stream after the lithography-polymerization step operates to conduct the particles through and out of the microfluidic device 112. A reservoir 134 is provided for collecting the output stream 136, which includes a population 138 of particles. As can be recognized, if only one transparent mask shape is employed, then the particle population is homogeneous, and preferably is mono-disperse.

The synthesized particles are rinsed in the reservoir or, e.g., taken by pipette into another container for rinsing. For example, the stream including the particle population is taken by pipette from the reservoir into an eppendorf tube, suspended in a buffer with a surfactant to prohibit agglomeration, and centrifuged to retrieve the particles from the stream. The particle population can then be employed for a selected application.

Figure 2A:
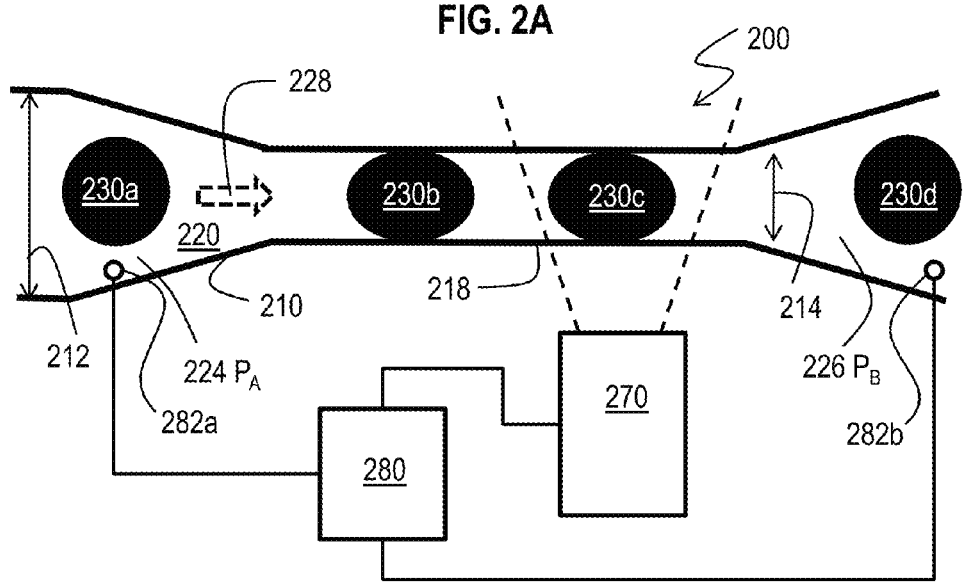
FIG. 2A is a block diagram that illustrates measurements of flexibility of particles, according to an embodiment.

According to various embodiments, the contents of the pre-polymer mixture 115 determine, at least in part, the flexibility and chemistry of the synthesized particles output by the system 100. FIG. 2A is a block diagram that illustrates measurements of flexibility of particles, according to an embodiment. These measurements allow the flexibility of the synthesized particles to be quantitatively determined based on the contents of the pre-polymer mixture. The measurements include a constricted channel 216 with a wide portion having a width 212 greater than the greatest dimension of particles to be measured and a constricted portion having a width 214 smaller than a greatest dimension of the particles to be measured. The thickness of the channel, perpendicular to the view of FIG. 2A, is no greater than the constricted width 214.

Particles 230a, 230b, 230c, 230d (collectively referenced hereinafter as particles 230) are suspended in a fluid 220 that is forced to flow in the direction indicated by dashed arrow 228 by a pressure gradient. In the constricted portion of the channel the particle might become deformed in order to pass through the constriction (in vivo such a constriction includes a small capillary through which the particle must pass) compared to the size or shape of the particle in the wide portion. For example, particles 230b, 230c are deformed while particles 230a and 230d are un-deformed.

The pressure difference to drive the particles through the constricted portion of the channel is taken as a measure of the flexibility of the particles. The greater the minimum pressure difference to drive the particles through the constricted portion, the less flexible, e.g., the stiffer, the particle. The pressure difference is determined by two or more pressure sensors 282a, 282b (collectively referenced hereinafter as pressure sensors 282) disposed at opposite ends of the constricted portion.

A separate measure of flexibility is based on the amount of deformation of the particle in the constricted portion of the channel 218, as described in more detail below with reference to FIG. 2C. The greater the deformation, the greater the flexibility (less stiff) the particle. To measure the deformation in some embodiments, an optical imager 270, such as an analog or digital camera or charge coupled device (CCD) array is directed to at least a portion of the constricted channel 218. These measurements combine the flexibility of the material of the particle, e.g., as measured or described by the elastic modulus of the material, with the flexibility imparted by the structure, e.g., rings, disks or crosses, among others.

The pressure sensor and image data are reported to a controller 280 to determine the pressure difference or deformation or both to characterize the flexibility of particles 230. In some embodiments the controller is an analog or digital computer with an analog to digital converter as desirable to convert digital or analog data from the pressure sensors 282 and imager 270. An example computer is described in more detail below with reference to FIG. 12.

Figure 2B:
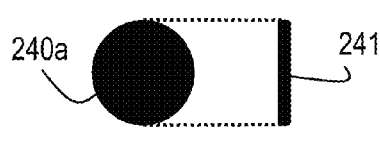
FIG. 2B is a block diagram that illustrates relative dimensions of a solid disk particle, according to an embodiment.
Figure 2C:
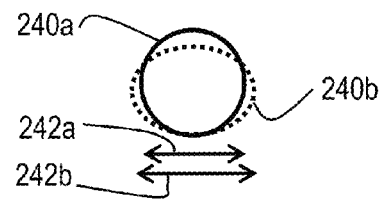
FIG. 2C is a block diagram that illustrates a measure of deformation of a particle, according to an embodiment.

FIG. 2B is a block diagram that illustrates relative dimensions of a solid disk particle, according to an embodiment. FIG. 2C is a block diagram that illustrates a measure of deformation of a particle, according to an embodiment. The un-deformed disk shape 240a and deformed disk shape 240b are collectively referenced herein as disk shape 240. The un-deformed disk shape 240a is circular in the widest dimension with a size represented by a diameter 242a and is a flattened oval or rectangle 241 in the shortest dimension with a shortest size represented by a thickness. The deformed disk shape 240a in the constricted portion of the channel is oval in the widest dimension with a size represented by a long axis 242b and a short axis perpendicular to the long axis. The percent deformation is determined as the percent elongation of diameter 242a to equal long axis 242b.

Figure 2D:
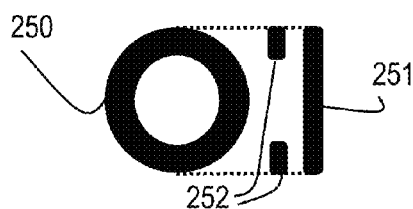
FIG. 2D is a block diagram that illustrates relative dimensions of a ring particle, according to an embodiment.

In some embodiments, a hollow shape is used for the particle to make them more flexible for a given composition. FIG. 2D is a block diagram that illustrates relative dimensions of a ring particle, according to an embodiment. The un-deformed ring shape 250 is a circular annulus in the widest dimension with a size represented by an outer diameter and an inner diameter. In some embodiments, the shape is a flattened oval or rectangle 251 in a side view of the shortest dimension with a shortest size represented by a thickness. A cross section closer to the center is shown as view 252.

Figure 2E:
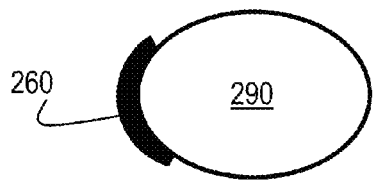
FIG. 2E is a block diagram that illustrates extent of contact for a flexible particle on a curved target object in a side view, according to an embodiment.

An advantage of selecting the flexibility of a particle is to tailor the particle for a particular use. A stiff spherical particle contacts a target at a limited contact region that approaches a single point. A disk can contact a flat target along an entire face. A flexible particle can contact even a curved target along an extended contact region. FIG. 2E is a block diagram that illustrates extent of contact for a flexible particle 260 on a curved target object 290 in a side view, according to an embodiment.

Figure 3A:
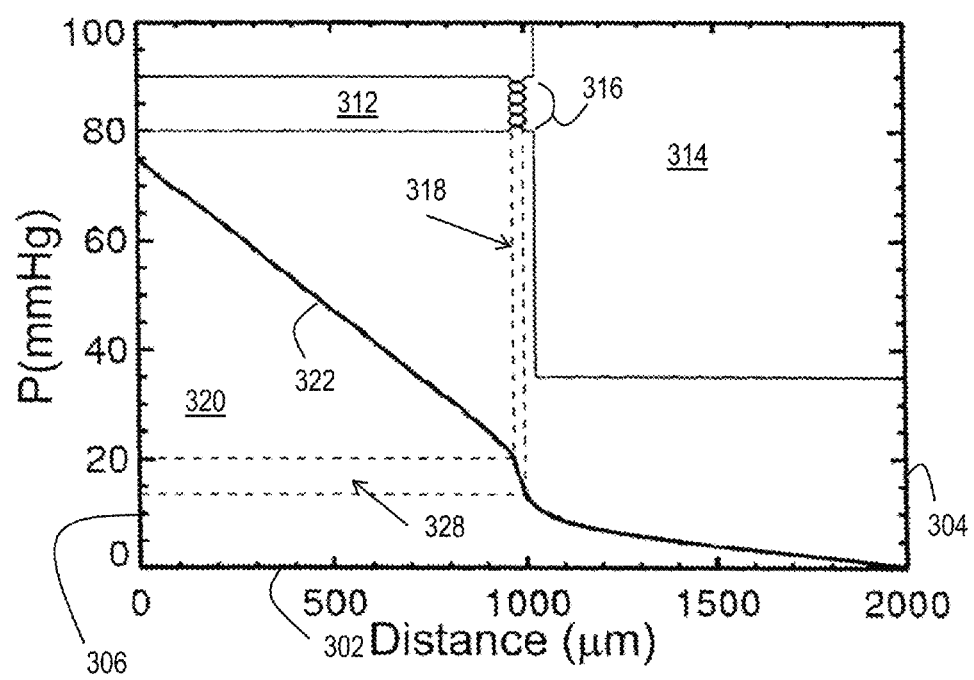
FIG. 3A is a graph that depicts micro-constrictions between chambers and depicts pressure to force particles through the micro-constrictions, according to an embodiment.

FIG. 3A is a graph that depicts micro-constrictions between chambers and depicts pressure to force particles through the micro-constrictions, according to an embodiment. A footprint of an illustrated measurement apparatus is plotted on a distance axis 302, showing distance in microns in a direction of flow and a perpendicular distance axis 304 of the same scale. The measurement apparatus includes an input chamber 312 and outflow chamber 314 separated by five constricted channels in a constricted region 316 in distance range 318 near 1000 μm. Particles of largest dimension size smaller than the width of chamber 312 but larger than the width of any of the constricted channels are forced from chamber 312 into chamber 314 through the region 316 of constricted channels.

The pressure change along the direction of flow is plotted in graph 320 that shares the distance axis 302 but uses a pressure (P) axis 306 in which pressure is measured in millimeters of Mercury (mmHg, 1 mmHg=133.3223684211 Newtons per square meter, also called a Pascal, Pa). The pressure trace 322 decreases uniformly and gradually along chamber 312 but decreases substantially in the distance range 318 of the constriction region by a pressure drop 328. The pressure drop 328 increases with the stiffness of the particle and decreases with the flexibility of the particle, and is used as a measure of stiffness/flexibility.

Figure 3B:
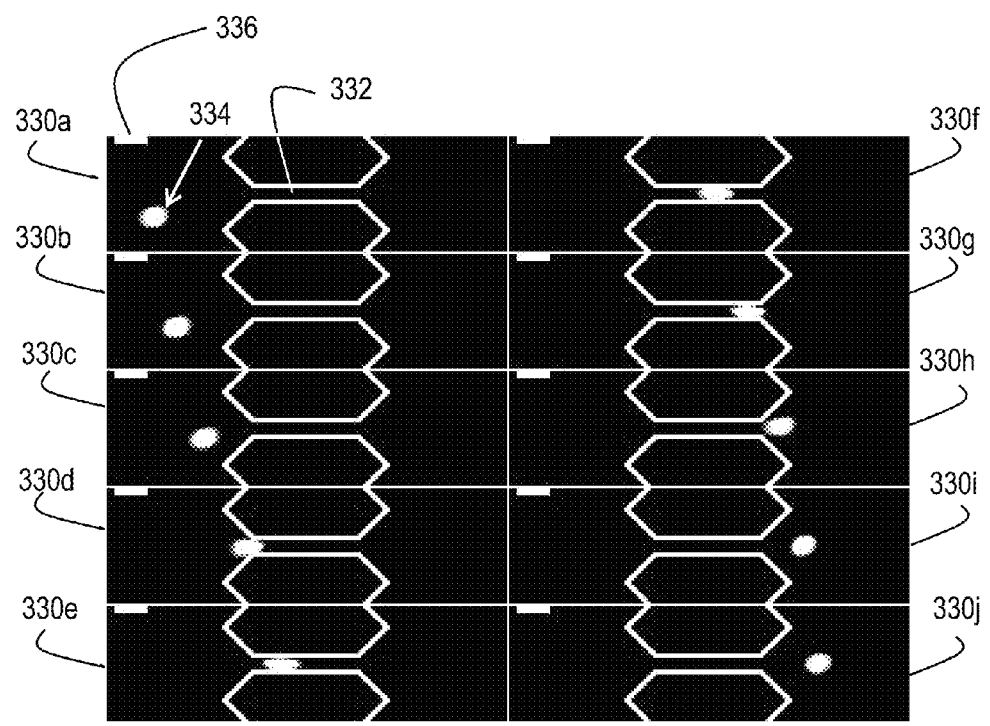
FIG. 3B is a sequence of micrographs that illustrates transport of a solid disk particle through a micro-constriction, according to an embodiment.

FIG. 3B is a sequence of micrographs that illustrates transport of a solid disk particle through a micro-constriction, according to an embodiment. The sequence includes images 330a, 330b, 330c, 330d, 330e, 330f, 330g, 330h, 330i, 220j separated in succession by 50 milliseconds (ms, 1 ms=$10^{-3}$ seconds). In each image is evident a scale bar 336 indicating a distance of 10 μm, constricted channel 332 and a single particle 334 as it is forced through the constriction. In the illustrated embodiment, the width and depth of the constricted channel cross section is 2 μm by 2 μm, about the size of a capillary. The diameter and thickness of the particle is about 8 μm by 2 μm, about the size of a red blood cell. As can be seen, the particle 334 deforms substantially but passes through the constriction, much as a red blood cell passes through a capillary. As described above, the measurement of this deformation is used as a separate measure of the flexibility of the particle.

Figure 4:
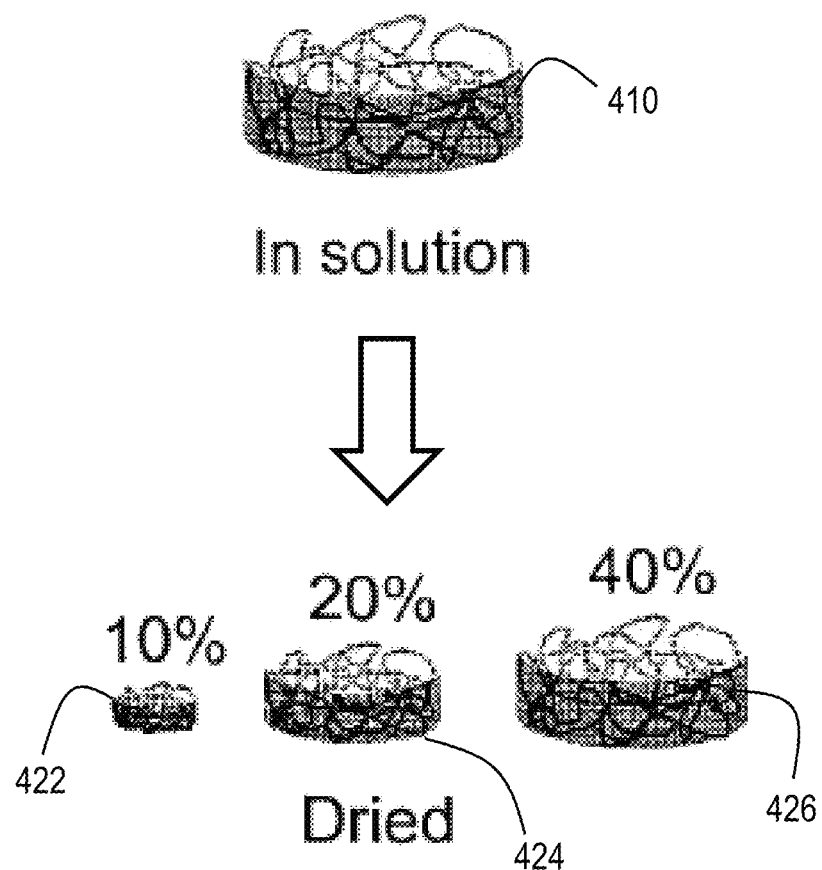
FIG. 4 is a block diagram that illustrates different extents of cross-linking in different microparticles, according to various embodiments.

It is well known that the mechanical strength of a hydrogel depends to a great extent on the number and nature of the cross-links present. The stiffness of particles was discovered also to be related to the amount of cross linking during polymerization among monomers in the pre-polymer mixture. The amount of cross linking affects hydrogel swelling, and flexibility, in solution. FIG. 4 is a block diagram that illustrates different extents of cross-linking in different microparticles, according to various embodiments. In solution a hydrogel particle is swollen as demonstrated by particle 410. When the particle is dried, e.g., all water is removed, the particle shrinks. A particle formed from a pre-polymer mixture with only 10% monomers shrinks more than particles formed from pre-polymer mixtures with 20% and 40% monomers, as indicated by particle 422, particle 424 and particle 426, respectively. The additional cross-linking is believed to lead to increased stiffness of the particle.

According to various embodiments, the stiffness of hydrogel particles is controlled over several orders of magnitude by varying the relative amounts of Poly(ethylene glycol) diacrylate (called PEGDA herein) and Poly(ethylene glycol) (called PEG herein) in the pre-polymer mixture. By using a pre-polymer with a higher proportion of the cross-linking active monomer agent (PEGDA), it was found to be possible to generate hydrogel particles with higher cross-linking densities that are more resistant to deformation. In the following embodiments Poly(ethylene glycol) diacrylate of molecular weight 700 (called PEGDA 700 herein) and Poly(ethylene glycol) of molecular weight 200 (called PEG 200 herein) are used. However, in other embodiments other molecular weights may be used, such as molecular weights in a range from about 50 to about 10,000. The presence of PEG without diacrylate, e.g., PEG 200, forms a semi-interpenetrating network to the resultant particle, which increases the effective surface area of the particle in solution.

FIG. 5A is a graph 510 that illustrates percent deformation of disk microparticles within micro-constrictions, according to various embodiments. The horizontal axis 512 represents PEGDA 700 percentage by volume in the pre-polymer mixture; and the vertical axis 514 represents percent deformation (e.g., ratio of deformed major axis to un-deformed diameter of the particle, expressed as a percentage). The particles tested were produced from a pre-polymer mixture of 20% by volume aqueous buffer, 15% by volume of 2-Hydroxy-2-methyl-1phenyl-propan-1-one (DAROCUR 1173) as a photo-initiator, and a first portion that includes 1% by volume Rhodamine-acrylate in PEG 200 (10 milligrams per milliliter, mg/mL, 1 mg=$10^{-3}$ grams, 1 mL=$10^{-3}$ liters) as a fluorescent label (called Rhod-A, herein) and relative fractions of PEGDA 700 and PEG 200 varied in order to tune the flexibility of the hydrogel particles. For convenience, this fraction of the contents is called the first fraction. PEG is a known bio-inert material so it does not interact with cells co-suspended in solution. Any buffer may be used. TE is a common buffer solution that consists of Tris (pH buffer) and EDTA (chelating agent) and is often used to prevent the degradation of nucleic acids by limiting the efficacy of nucleases. The data points 516 show that as the percent PEGDA 700 increases to 20% by volume, the corresponding percent deformation decreases from about 180% to about 120%.

FIG. 5B is a graph 520 that illustrates pressure differential to transport disk microparticles through micro-constrictions, according to various embodiments. The horizontal axis 512 represents PEGDA 700 percentage by volume in the pre-polymer mixture as in FIG. 5A; and the vertical axis 524 represents pressure difference (e.g., 328) across the constricted region in millimeters of Mercury (mmHg). The data points 526 show that as the percent PEGDA 700 increases from 10% by volume to 40% by volume, the corresponding pressure difference increases from about 0.9 mmHg to about 200 mmHg, over two orders of magnitude. At low percentages of PEGDA 700, particles easily pass through constrictions under application of moderate pressures such as those found in natural organisms; such pressures are called physiological pressures. At high percentages of PEGDA 700, the particles are difficult or impossible to pass through contractions under application of moderate pressures, and demand very high pressure differences.

In another set of embodiments, acrylic acid was included in the first fraction of the pre-polymer mixture to provide a functional group, such as a carboxyl group, that allows the particles to bind to one or more molecules each with an affinity for one or more targets (called herein "target affinity molecules" such as antibodies or receptors or antigens), thereby imparting variations in the chemical properties or functionality of the particles, as described in more detail below. Acrylic acid (prop-2-enoic acid) is an organic compound with the formula CH2CHCO2H. It is the simplest unsaturated carboxylic acid, consisting of a vinyl group connected directly to a carboxylic acid terminus. Acrylate chemistries for modifying the surface of a particle are well known in the art. In these embodiments, the pre-polymer mixture includes 20% by volume aqueous buffer and 15% by volume of DAROCUR 1173 as described above. However, a different first fraction can also be used, for example one that includes: 1% by volume Rhod-A as a fluorophore; acrylic acid (AA) in concentrations from about 1% to about 40% to alter the chemical properties of the particles; and variable relative fractions of PEGDA 700 and PEG 200 in order to tune the flexibility of the hydrogel particles. In some embodiments, other acrylate (AR) chemistries such as biodegradable cross-linker molecules are added to create colloids that degrade over time, which is an important consideration for drug delivery applications. In embodiments with Rhod-A or AA added to the pre-polymer mixture, the percentage of PEG (e.g., PEG 20) was lowered to compensate in the first fraction.

Certain embodiments are directed to biodegradable hydrogel particles. Applicants have described one such hydrogel, a diacrylated triblock copolymer composed of poly(ethyleneglycol) (PEG) and poly(lactic acid) (PLA), that has been extensively characterized as a degradable tissue scaffold. (See Hwang, D. K., Oakey, J., Toner, M., Arthur, J., Anseth, K., Lee, S., Zeiger, A., Van Vliet, K., and Doyle, P. S., "Stop-Flow Lithography for the Production of Shape-Evolving Degradable Microgel Particles", *J. Am. Chem. Soc.*, v131, pp 4499-4504, 2009, the entire contents of which are hereby incorporated by reference as if fully set forth herein). Diacrylate PLA-b-PEG-b-PLA is a highly cross-linked, water-swollen gel network that degrades through the isotropic hydrolysis of hydrolytically labile ester linkages in the PLA block. As degradation proceeds, water content of the gel increases exponentially until complete dissolution of the network is reached. The products of degradation are poly(acrylic acid), PEG, and lactic acid. Other biodegradable cross linking reagents can be used in the present invention, including those described in Buisman, G. J. H., "Biodegradable binders and cross-linking agents from renewable resources," *Journal Surface Coatings International Part B: Coatings Transactions*, Springer Boston, v82, No. 3, March, 1999, the entire contents of which are hereby incorporated by reference as if fully set forth herein, except as the terminology conflicts with that explicitly set forth herein.

The presence of AA in the reaction results in free carboxyl groups cross-linked into the backbone of the polymers in the particle. Carboxyl chemistry is a well established way to functionalize colloids with proteins and antibodies. In various embodiments, the particle surfaces and pores can be modified using any basic physical chemical method, including basic organic and inorganic coupling chemistries known in the art, both with or in place of AA.

The sizes and shapes of the particles were defined independently by photo-masks and the polymerization was done using SFL. For the experimental results presented next, four shapes were polymerized, e.g., disk and ring shaped particles as shown in FIG. 2B and FIG. 2D, respectively, with about 8 µm outer diameters and 2 µm thicknesses. These shaped particles were forced through microfluidic contractions with channel dimensions of 4 µm×4 µm in cross-section, on the order of capillaries in a human vascular system.

The pressure difference (e.g., pressure difference 328) required to push the shaped particles through the constricted regions was plotted as a function of the concentration of reactive PEGDA 700 in the pre-polymer solution. FIG. 5C is a graph 530 that illustrates pressure differential to transport four different shaped microparticles through micro-constrictions, according to various embodiments. The horizontal axis 532 is PEGDA 700 concentration in percent by volume; and the vertical axis is pressure difference (e.g., 328) across the constricted region in mmHg. Data points 536a for disk-shaped particles, data points 536b for ring shaped particles, data points 536c for cross shaped particles and data points 536d for S shaped particles are shown. By changing particle geometry slightly (e.g., between disk shapes and S shapes) and changing the concentration of reactive PEGDA 700, the flexibility of the resulting hydrogel particles with variable chemistry represented by the AA content was changed about four orders of magnitude. The minimum pressure differences of less than about 1 mmHg are physiological while the stiffest particles demand pressures of hundreds of mmHg. This ability to tune the mechanical properties of colloidal particles while maintaining independent control over their chemistry has not been previously demonstrated.

Observations of images indicated that stiff disk shaped particles unable to pass through under significant pressure drops fold into "taco" shapes within a contraction. Ring shaped particles exhibit enhanced flexibility proportional to bending area. For example, 8 µm diameter disk shaped particles illustrated herein bend along an 8 µm line, while rings of the same outer diameter merely bend along two 2 µm line segments, and experience about half the stiffness (twice the flexibility). Table 1 shows some pressure differentials measured for various particles.

TABLE 1

Variation of flexibility with shape and PEGDA content

| Shape | PEGDA 700 DA content (percentage by volume) | Stiffness (pressure drop required for passage, mmHg) |
|---|---|---|
| Disks | 10 | 3.0 |
| | 12 | 17 |
| | 15 | 23 |
| | 20 | 44 |
| | 30 | 107 |
| | 40 | 330 |
| Rings | 10 | 0.9 |
| | 12 | 2.6 |
| | 15 | 3.6 |
| | 20 | 8.3 |
| | 30 | 40 |
| | 40 | 130 |
| Crosses | 10 | 0.3 |
| | 12 | 1.4 |
| | 15 | 2.5 |
| | 20 | 6.3 |
| | 30 | 19 |
| | 40 | 72 |
| S-Shapes | 10 | 0.05 |
| | 12 | 0.33 |
| | 15 | 1.05 |
| | 20 | 3.6 |
| | 30 | 8.2 |
| | 40 | 16 |

FIG. 6 is a flowchart 600 that illustrates a method to produce and use tunable particles, according to an embodiment. Although steps are shown in a particular order in FIG. 6 and subsequent flow diagrams FIG. 7B, FIG. 9 and FIG. 10, for purposes of illustration, in other embodiments steps, or portions thereof, are performed in a different order or overlapping in time, performed in series or parallel, or one or more steps are omitted or one or more other steps are added, or the method is changed in some combination of ways. In some embodiments, one or more steps or portions thereof are performed at least in part by a digital computer described in more detail below with reference to FIG. 12.

In step 603 the pre-polymer content for the desired stiffness of the particles for the intended purpose is selected. For example, if the particles are to be used in a living organism with constrictions smaller than the size of the particles (such as capillaries of a vascular system) then the flexibility of particles that pass such constrictions at physiological pressures is chosen. In another example, if the particle is used in flow cytometry, then stiffness that allows particles to retain a desired shape at those pressures is selected. When the desired stiffness/flexibility is selected, the content of the pre-polymer mixture, e.g., the percent and molecular weight of PEGDA that provides that stiffness is determined, e.g., based on historical data, such as data in graph 520 or in graph 530. In some embodiments, the graph is extended to multiple molecular weights, saved as machine readable data and a machine interpolation or other determination is performed. Thus, a percentage of PEGDA is selected to impart a desired stiffness to the particles.

The percent volume of the first fraction, that includes PEG and PEGDA plus any other components such as AA, is from about 30% to about 95% of the total volume, preferably 65%. The molecular weight of the monomer PEGDA can vary from the minimum to form gels, about 10%, to a maximum that allows sufficient photo-initiator, about 95%. A preferred embodiment described herein uses PEGDA 700, however PEGDA of any molecular weight can be used either together with or instead of PEGDA 700. The amount of PEGDA to use will be determined as was described above for PEGDA 700 using historical data. o In some embodiments, step 603 includes performing further measurements with the apparatus of FIG. 2A or FIG. 3A for a large variety of particle shapes and sizes, constriction sizes and concentrations and molecular weights of PEGDA to produce of family of curves that predict stiffness over four or more orders of magnitude. The interpolation is performed on the larger family of curves. A computer capable of implementing this step in some embodiments is described in more detail below with reference to FIG. 12.

In step 605 the pre-polymer content is adjusted to compensate for the addition of any other components to the first fraction that facilitate fluorescent particle detection. For example, if the particles are to be detected by fluorescence, then a content for a fluorophore, such as 1% by volume Rhod-A is selected. The amount of PEG is decreased by 1% to compensate. In some embodiments, fluorescent detection is not desired and step 605 is omitted. In other embodiments other agents that facilitate particle detection can be used.

In step 607, the pre-polymer content is adjusted to compensate for the optional addition of active substances added to the first fraction to achieve a desired particle chemistry for the intended purpose. Such active substances include any drugs such as therapeutic agents, AA or AR In some embodiments, step 607 is omitted.

For convenience, the combined contents selected in steps 603, 605 and 607 are called the first fraction. For example, in step 609 about 20% by volume aqueous buffer and 15% by volume of DAROCUR 1173 as described above are combined with 65% by volume of the first fraction. For the data shown in FIG. 5C and a choice of intermediate flexibility for the particles, the first fraction include 1% by volume Rhod-A, 10% by volume acrylic acid, 20% by volume PEGDA 700 to impart an intermediate flexibility and the remaining 34% by volume PEG 200.

In step 609, the composition of the remaining fraction of the pre-polymer mixture is determined. The remaining fraction includes a buffer and photosensitive ingredient, also called a photo-initiation ingredient. The remaining fraction is added to the first fraction the contents of which were selected in steps 603 and 605 and 607. In step 611, the size and shape of the particles are selected, e.g., by selecting a particular microfluidic device 112 capable of producing particles of the desired thickness and a photo-mask for the desired size and shape in the length and width of the particles. For example, in some embodiments, photo-masks for rings are selected over photo-masks for disks for increased flexibility in the resulting particles.

In step 613, particles with the desired independently selected flexibility, detectability, chemistry, size and shape are produced using SFL by introducing the pre-polymer mixture formed in step 609 to a SFL system, such as depicted in FIG. 1. In some embodiments, step 613 includes one or more steps to incubate the particles with solutions that interact with the products of the contents selected in step 607 to impart target affinity to the particles, as described in more detail below. The molecules in solution that bind to carboxyl groups of the acrylic acid to impart the target affinity are called the target affinity molecules.

Figure 7A:
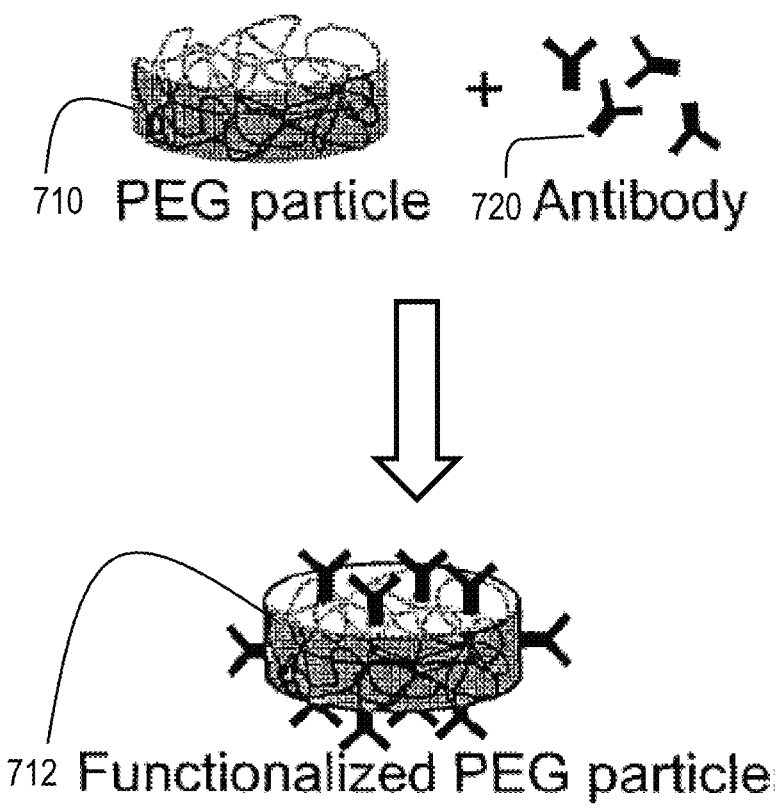
FIG. 7A is a block diagram that illustrates functionalization of a particle, according to an embodiment.

In step 615, the particles are administered to or contacted with a "subject" (an animal, a biological sample or article of manufacture). As stated above, in some embodiments, during step 613, a particle is incubated in solution with target affinity molecules. For example, in embodiments with acrylic acid (AA) included in the pre-polymer mixture, the polymerization produces particles with carboxyl groups. The carboxyl groups can bind to proteins using carboxylic acid-amine chemistry. FIG. 7A is a block diagram that illustrates functionalization of a particle, according to an embodiment in which the hydrogel particles 710 (also called PEG particles) produced in step 613 are incubated in solution with one or more antibodies, such as antibody 720. The antibodies bind to the carboxyl groups to form functionalized hydrogel particles 712, herein also functionalized PEG particles. The antibody has an affinity for a corresponding antigen, which is the target. Thus the antibody-functionalized particle 712 will have an affinity for the same antigen, allowing the functionalized particle 712 to bind to the target antigen.

Figure 7B:
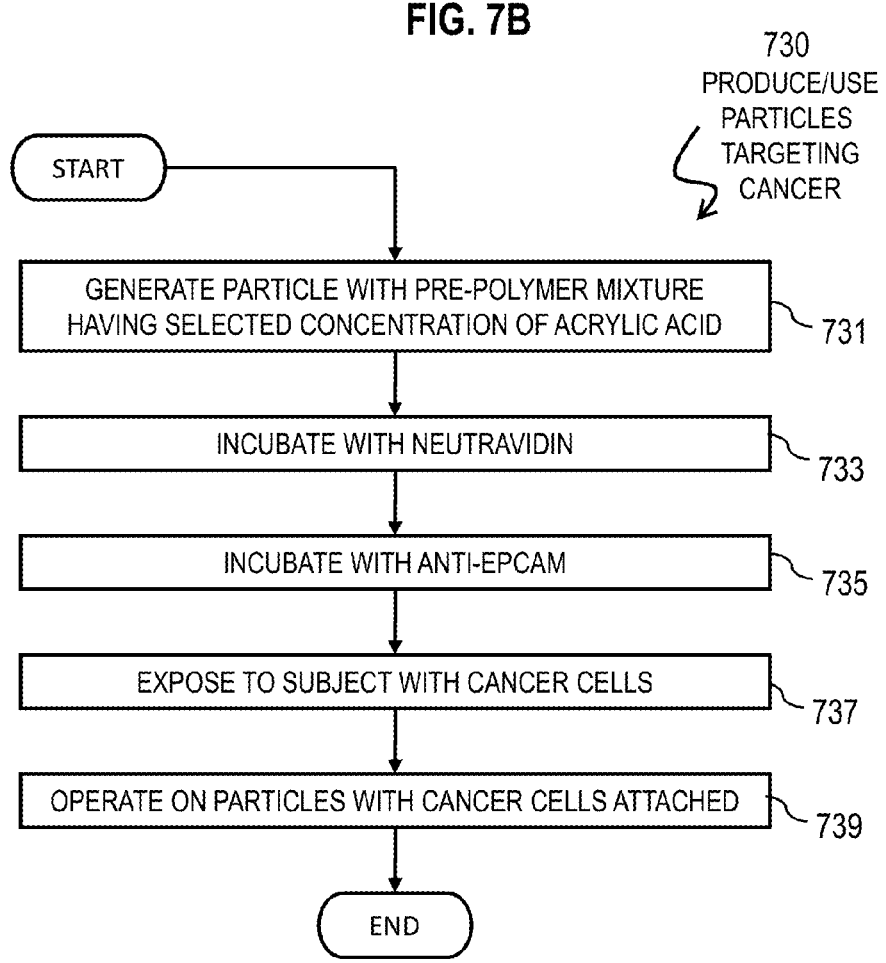
FIG. 7B is a flowchart that illustrates a method to produce and use particles targeting cancer cells, according to an embodiment.

FIG. 7B is a flowchart that illustrates a method 730 to produce and use particles targeting cancer cells, according to an embodiment. Method 730 is a particular embodiment of steps 613 and 615 described above, using multiple incubations. In step 731, particles are produced using a pre-polymer mixture having selected concentration of acrylic acid (e.g., 10% by volume).

In step 733, the particles are incubated with NeutrAvidin or streptavidin, which bind very strongly to biotin, to produce conditioned particles in which the NeutrAvidin or streptavidin is linked to the particle via the carboxyl groups. As is known in the art, biotin can be attached to a molecule of interest (e.g. a protein), and this biotinylated molecule will bind strongly to the NeutrAvidin or streptavidin.

In step 735, the particles conditioned with NeutrAvidin or streptavidin are incubated with the biotinylated target affinity molecule anti-EpCAM to produce functionalized particles that preferentially adhere to carcinomas expressing surface EpCAM. that The antigen EpCAM is known to be expressed on the surface of various types of carcinomas (cancer cells), In step 737, the functionalized particles are administered to a an animal with cancer, or contacted with a biological sample such as the blood or tissue of a diseased patient in vivo or in vitro. In step 739 an operation is performed on the particles attached to the cancer cells. For example, the particles can be filtered out of the blood stream thereby removing blood-borne cancer cells that have bound to the particles. In other embodiments, the particles taken up by the targeted cancer cells release a cell killing agent, such as a chemotherapy agent, that kills the targeted cells.

Steps 731, 733 and 735 are performed during step 613, described above; and step 737 is performed during step 615, described above. Step 739 is also included in step 615 in some embodiments.

Figure 7C:
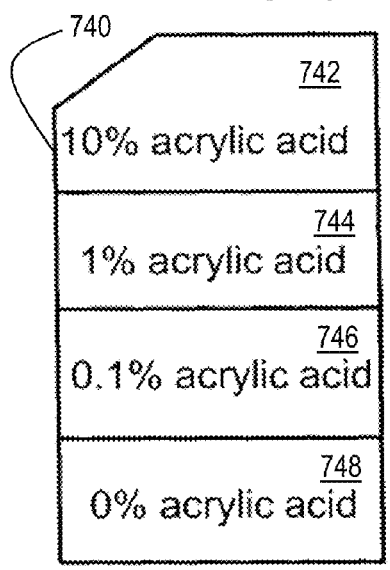
FIG. 7C is a block diagram that illustrates a particle produced with different percentages of acrylic acid for tunable chemical properties, according to an embodiment.

To demonstrate the ability to impart the particles with independently selected chemical properties, the amount of acrylic acid in the pre-polymer mixture and the incubation times were varied to make the anti-EpCAM particles described above. FIG. 7C is a block diagram that illustrates a particle 740 produced with different percentages of acrylic acid for tunable chemical properties, according to an embodiment. A first portion 742 of the particle is formed from a pre-polymer mixture including 10% acrylic acid. A second portion 744 is formed from a different pre-polymer mixture having 1% acrylic acid; and a third portion 746 is formed from a different pre-polymer mixture having 0.1% acrylic acid. The fourth portion 748 is formed from a different pre-polymer mixture having no acrylic acid. Such particles are readily formed using SFL by flowing different mixtures in adjacent streams of width small compared to the area illuminated by the photo-mask, light and lens system, as described in more detail in Doyle I.

The particles were separated into three groups named A, B, and C. During step 733, each group of particles was incubated for 45 minutes at room temperature in a solution of NeutrAvidin with a different concentration. Group A was incubated with a solution having a concentration of 25 micrograms per mL ($\mu$g/mL, 1 $\mu$g=$10^{-6}$ grams) NeutrAvidin; group B was incubated with a solution of 50 $\mu$g/mL NeutrAvidin; and group C was incubated with a solution of 100 $\mu$g/mL NeutrAvidin. Thus group C is expected to have the most binding with the biotinylated antigen anti-EpCAM.

During step 735, each of the three groups was incubated for 30 minutes at 37° C. with a solution having a concentration of 10 $\mu$g/mL anti-EpCAM. During step 737, each of the three groups was then incubated for one hour at room temperature with a solution having cancer cells that express the protein H1650 EpCAM.

Figure 7D:
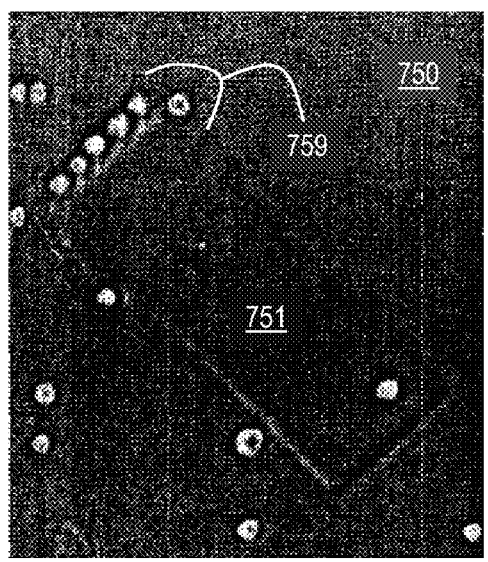
FIG. 7D through FIG. 7F are images that illustrate effects of different incubation times in presence of a compound having affinity for cancer cell targets, according to various embodiments.
Figure 7E:
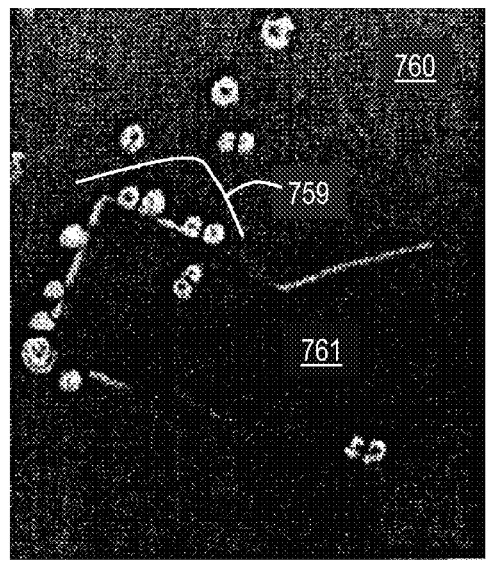
Figure 7F:
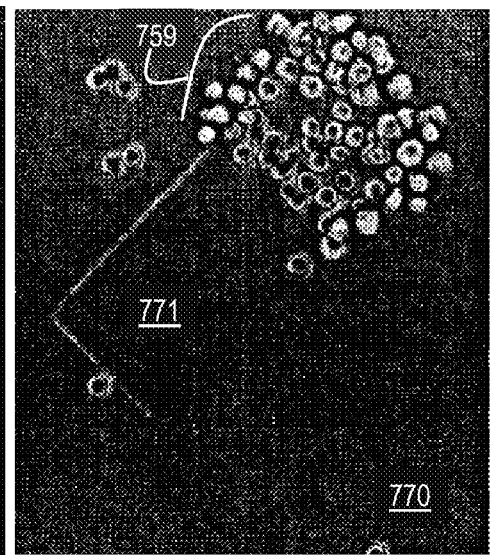

FIG. 7D through FIG. 7F are images that illustrate effects of different incubation times in presence of a compound having affinity for cancer cell targets, according to various embodiments. In FIG. 7D, the image 750 shows a particle 751 from group A. Cancer cells 759 have attached to the first portion 742 of the particle 751. The 10% acrylic acid of the pre-polymer mixture was effective in providing carboxyl groups that could bind to the NeutrAvidin which binds to the antigen that has the affinity for the cancer cells, even for the low concentration of NeutrAvidin in group A. In FIG. 7E, the image 760 shows a particle 761 from group B. Cancer cells 759 again have attached to the first portion 742 of the particle 761. In FIG. 7F, the image 770 shows a particle 771 from group C. Cancer cells 759 have attached to both the first portion 742 and the second portion 744 of the particle 771. The 1% acrylic acid of the pre-polymer mixture was effective in providing carboxyl groups that could bind to the NeutrAvidin which binds to the antigen that has the affinity for the cancer cells, at least for the high concentration of NeutrAvidin in group C.??

Figure 8A:
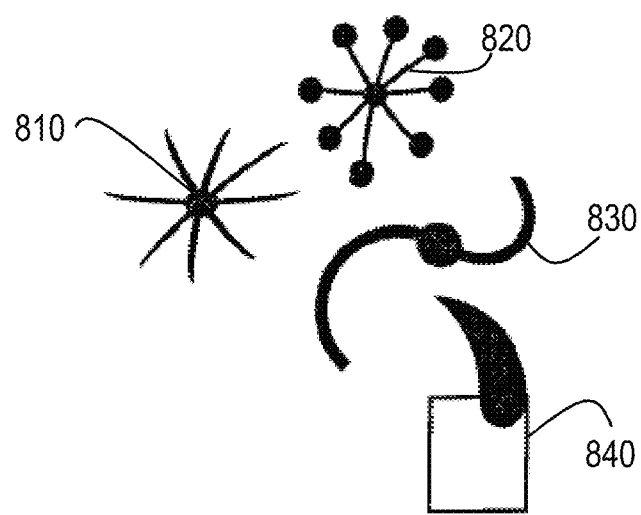
FIG. 8A is a block diagram that illustrates different particle shapes having high target interactions but low hydrodynamic resistance, according to various embodiments.
Figure 8B:
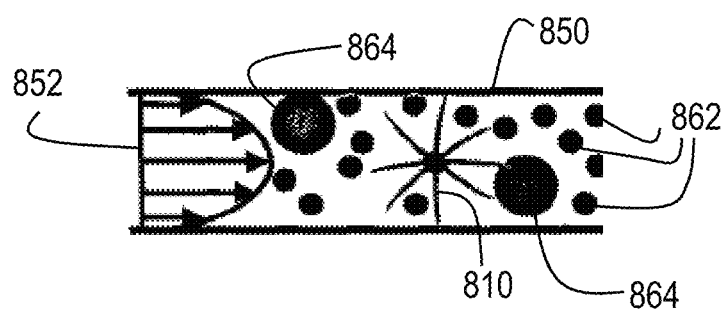
FIG. 8B is a block diagram that illustrates a particular shaped particle in a reaction chamber, such as a blood vessel, according to an embodiment.

In some embodiments, the size and shape of microparticles are selected so that the particles move deterministically in suspension flow. For example, particles are chosen that are physically large but are hydrodynamically small. FIG. 8A is a block diagram that illustrates different particle shapes having high target interactions but low hydrodynamic resistance, according to various embodiments. Shapes 810, 820, 830 and 840 are depicted. The high target interaction comes from the physical extent of the particles, but the low resistance to flow comes from large spaces in these shapes. Any of these shapes may be produced using SFL by selecting appropriate photo-masks in step 611, as described above. FIG. 8B is a block diagram that illustrates a particular shaped particle in a reaction chamber 850, such as a blood vessel, according to an embodiment. The fluid flow in the chamber 850 is represented by the velocity vectors 852. Flow is slow along the chamber wall and faster as distance from the wall increases. Entities in the flow are represented by small objects 862 and large objects 864. A hydrogel particle 810 is large enough to detect all the objects in the chamber, but by virtue of the spaces at the edges of the particle is not unduly dragged by the slow moving fluid at the chamber wall.

FIG. 9 is a flowchart that illustrates a method 900 to produce and use particles targeting proteins, including nucleic acids, according to an embodiment. Method 900 is a particular embodiment of method 600, described above.

In step 903, the content of PEGDA 700 is selected for imparting a desired stiffness of the resultant particles. For example, a target stiffness is selected from graph 530, e.g., by numerical interpolation using a computer and any known interpolation procedure. In some embodiments, step 903 includes performing further measurements with the apparatus of FIG. 2A or FIG. 3A for a large variety of shapes and particle sizes and constriction sizes and concentrations of PEGDA 700 to produce of family of curves to predict stiffness over three or more orders of magnitude. The interpolation is performed on the larger family of curves. An initial PEG 200 percentage is determined to bring the first fraction to a desired first fraction amount in the range from about 30% to about 95%, e.g., about 65% by volume of the total mixture. Step 903 is a particular embodiment of step 603.

In step 905, the content of Rhod-A is selected for imparting fluorescent detectability of the resultant particles. The initial content of PEG 200 is reduced by like amount to compensate. Step 905 is a particular embodiment of step 605, and is omitted in some embodiments.

In step 907, the content of acrylic acid is selected for imparting free carboxyl groups in the resulting particles. In step 909 the content of acrylate is selected for imparting bio-degradation of the particle after it is used (post-use) in step 923, described below. The remaining content of PEG 200 is reduced by like amount to compensate for both the acrylic acid and acrylate content. Steps 907 and 909 are a particular embodiment of step 607, and either or both are omitted in some embodiments.

In step 911, the content of PEG 200 is selected to bring the first fraction to the desired first fraction amount. In step 913, the mixture is formed by adding the first fraction to the buffer and photo-initiation ingredient, e.g., 10% by volume buffer and 15% by volume of DAROCUR 1173, respectively. Steps 911 and 913 are a particular embodiment of step 609.

In step 915, the thickness is determined for the chamber of the microfluidic device where the mixture is to be polymerized, e.g. in microfluidic device 112, which limits the thickness of particles formed therein. The intensity and uniformity of the illumination is also determined so the light penetrates far enough into the pre-polymer mixture to polymerize a thick enough layer of the pre-polymer mixture to form particles of the desired thickness and uniformity of thickness. In step 917 a photo-mask is selected that imparts the desired size and shape to the wide dimension of the particle. For example, a disk shaped photo-mask is selected to produce particles with a flat surface for improving contact with a flat surface in a target. Steps 915, 917, are particular embodiments of step 611.

In step 919, the monomers in the pre-polymer mixture are polymerized to produce particles using SFL. In step 921, the particles are incubated with a solution of a compound or molecule that has an affinity for a target (called a target-affinity compound) to produce functionalized particles. In some embodiments, step 921 includes incubation with solutions of other compounds before or after incubating with a solution of the target-affinity compound, e.g., to produce conditioned particles. Steps 919 and 921 are particular embodiments of step 613, and step 921 is omitted in some embodiments.

In step 923 particles are administered to a subject. For example, the particles are introduced to an animal or contacted with a biological sample taken from a patient. Step 923 is a particular embodiment of step 615.

In some embodiments, particles are formed that have the mechanical properties of red blood cells (RBC) in passing through the capillaries of living organism. These particles are said to mimic RBCs. FIG. 10 is a flowchart that illustrates a method 1000 to produce and use particles that mimic RBCs, according to an embodiment. Method 1000 is a particular embodiment of method 900. In step 1003, a PEGDA 700 content is selected that provides the stiffness of RBCs. For example, rings with the stiffness and capillary passage of RBCs can be produced with a PEGDA 700 content of 10% by volume (this implies an initial PEG 200 content of 55% by volume). In some embodiments, other molecular weights are selected for the PEGDA content, based on historical experience or data.

In step 1005, the content of Rhod-A (e.g., 1% by volume) is selected for imparting fluorescent detectability of the resultant particles. The initial content of PEG (e.g., PEG 200) is reduced by like amount to compensate (e.g., reduced to 54% by volume). Step 1005 is omitted in some embodiments.

In step 1007, the content of acrylic acid is selected for imparting free carboxyl groups in the resulting particles. In step 1009 the content of acrylate is selected for imparting bio-degradation of the particle after it is used (post-use) in step 1023, described below. The remaining content of PEG (e.g., PEG 200) is reduced by like amount to compensate for both the acrylic acid and acrylate content. For example, in some embodiments, steps 1007 and 1009 are omitted, and the PEG 200 content remains at 54% by volume.

In step 1011, the content of PEG is selected to bring the first fraction to a desired amount (e.g., PEG 200 is selected to be 54% to bring the first fraction amount to about 65% by volume); and the mixture is formed by adding the first fraction to the buffer and photosensitive ingredient, e.g., 10% by volume buffer and 15% by volume of DAROCUR 1173.

In step 1013, the thickness is determined for the chamber and intensity and uniformity of the illumination is determined to form particles of RBC thickness, about 2 μm. For example, the chamber thickness is 4.5 μm and the illumination is provided by a 100 W HBO lamp as a light source shone through a wide UV excitation filter set (11000v2: UV, Chroma) and a 40× objective lens for a duration of 50-150 ms. In step 1015 a photo-mask is selected that imparts the desired size and shape to the wide dimension of the particle. For example, a ring shaped photo-mask that projects to an outer diameter of 8 μm and inner diameter of 4 μm is selected to produce particles that mimic RBC.

In step 1017, the monomers in the pre-polymer mixture are polymerized to produce particles using SFL. In step 1019, the particles are incubated with a solution of a target-affinity compound to produce functionalized particles. Step 1019 is omitted in an illustrated embodiment.

In step 1021 the particles are introduced into the bloodstream of an animal, such as a patient.

Thus are synthesized polymeric hydrogel microparticles that are of comparable size and shape to red blood cells (RBCs) and have tunable deformability resulting in bio-mimetic properties. These particles, like RBCs, possess the ability to deform and squeeze through small contractions in the circulation. The pressure drop required for passage is less than about 1 mmHg. In these embodiments, the size and pressure drop of the system are similar to conditions in vivo.

Figure 11A:
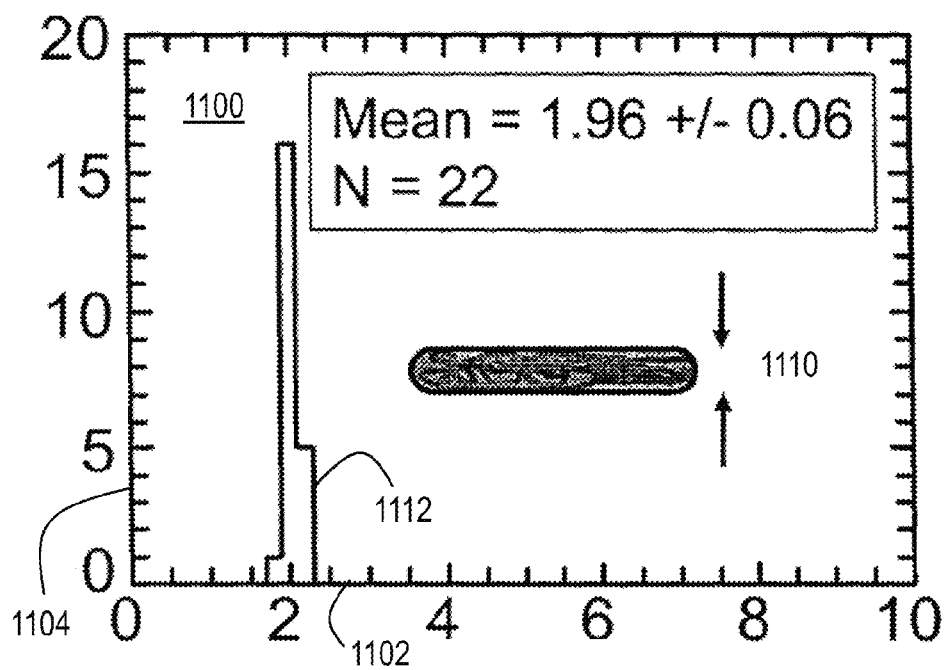
Figure 11B:
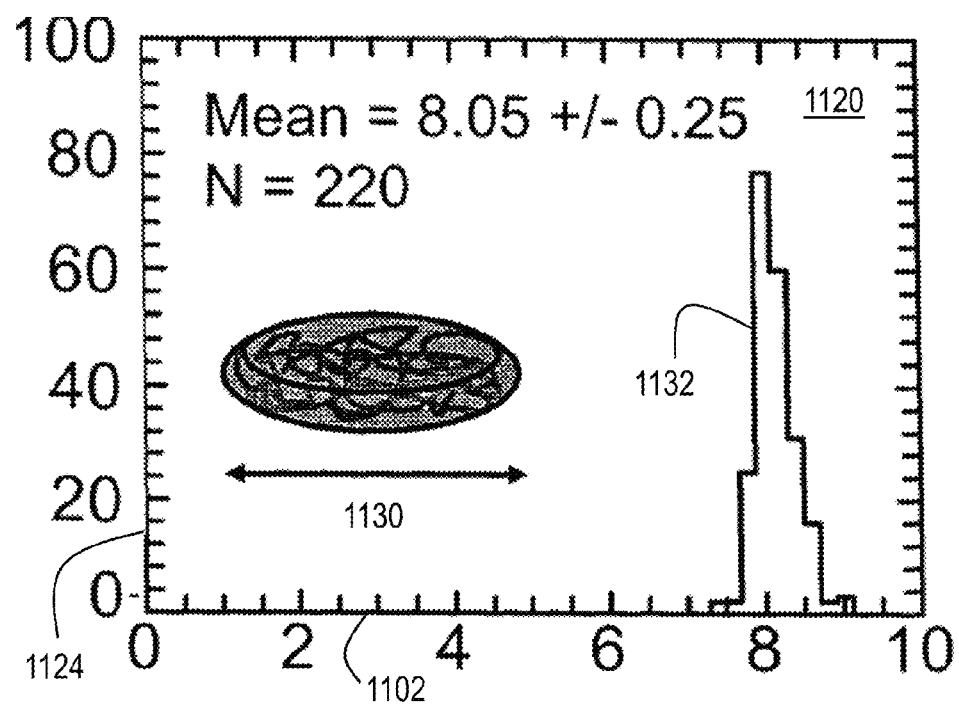

FIG. 11A and FIG. 11B and FIG. 11C are graphs that illustrate the production of particles that mimic red blood cells, according to various embodiments. FIG. 11A is a histogram 1100 illustrating a distribution of particle thicknesses 1110. The horizontal axis 1102 is distance in μm, divided into bins of about 0.2 μm; and the vertical axis 1104 is count from a population of 22 particles (a small population because many more particles lay flat than lay on their edge). The distribution is very narrow, showing good control of particle thickness, at 1.96±0.06 μm. FIG. 11B is a histogram 1120 illustrating a distribution of particle diameters 1130. The horizontal axis 1102 is distance in μm, divided into bins of about 0.2 μm; and the vertical axis 1124 is count from a population of 220 particles. The distribution is very narrow, showing good control of particle diameter, at 8.05±0.25 μm. These particles were measured to have diameter and thickness approximately the size of a RBCs. FIG. 11D is an image 1160 that illustrates a particle 1170 among red blood cells 1164, according to an embodiment. The distance bar 1162 indicates 10 μm in the image.

Ring shaped particles of RBC size were also produced. FIG. 11C is a histogram 1140 illustrating a distribution of ring-shaped particle outer diameters. The horizontal axis 1102 is distance in μm, divided into bins of about 3 μm; and the vertical axis 1144 is count from a population of 80 particles. The distribution is still narrow, showing good control of particle diameters, at 7.99±0.3 μm.

These data demonstrate the ability to controllably tune the deformability of hydrogel microparticles that are similar in size and shape to RBCs. In order to quantify the deformability of the particles, they were driven through microfluidic contractions with cross-sections of 2 μm×3 μm and 4 μm×4 μm (each dimension smaller than the largest dimension of the particles). By varying the amount of reactive PEGDA 700 in the pre-polymer mixture, e.g., an oligomer solution, identically sized objects with drastically different mechanical properties were produced. The most flexible particles exhibited similar behavior to RBCs when forced through narrow constrictions at physiological pressures.

Particles of these sizes and flexibilities can be used in in vivo drug delivery or diagnostics. Previously, there was no known way to synthesize colloids that are large enough to stay in circulation (not absorbed into tissue like nanoparticles with largest dimension on the order of 0.5 μm and less) but flexible enough to pass through the narrow passages found in the vascular system, for example through small capillaries. The particles described here are capable of performing that function. The ring shaped particles were able to pass through 4 μm contractions under a pressure difference of 0.7 mmHg, which are the lower limits of size and pressure that are found in the human vascular system. These new particles can be functionalized with a drug molecule or a target affinity molecule, and introduced into circulation where they can survive (or even degrade) over a long time rather than being cleared or absorbed into tissue like the current nanoparticle drug delivery vehicles.

The new hydrogel particles presented here surpass the limitations of existing colloidal materials used in a variety of industries. The ability to tune the flexibility of the colloids while maintaining independent control over their size/shape and chemistry enables better solutions to current in vitro and in vivo diagnostics as well as new material additives for many products. The established technology of SFL enables the easy manufacture of these hydrogel particles and their wide range of properties allow for such particles to make inroads into any field where colloids are currently used. Furthermore, the range of flexibilities demonstrated for these materials encompasses the entire range of flexibilities demonstrated by all other techniques for manufacturing colloids—indicating that these hydrogel particles provide not only new properties but also can replace existing colloid technology for many applications.

The new hydrogel particles can be used in drug delivery and diagnostic applications in the biomedical field. They can also be used to improve material properties of food, cosmetics, paints, and any other product which currently uses colloid technology. The colloids can also be used for basic research purposes to increase understanding of the role of mechanical properties in colloidal self-assembly and interactions, among other uses.

Figure 12:
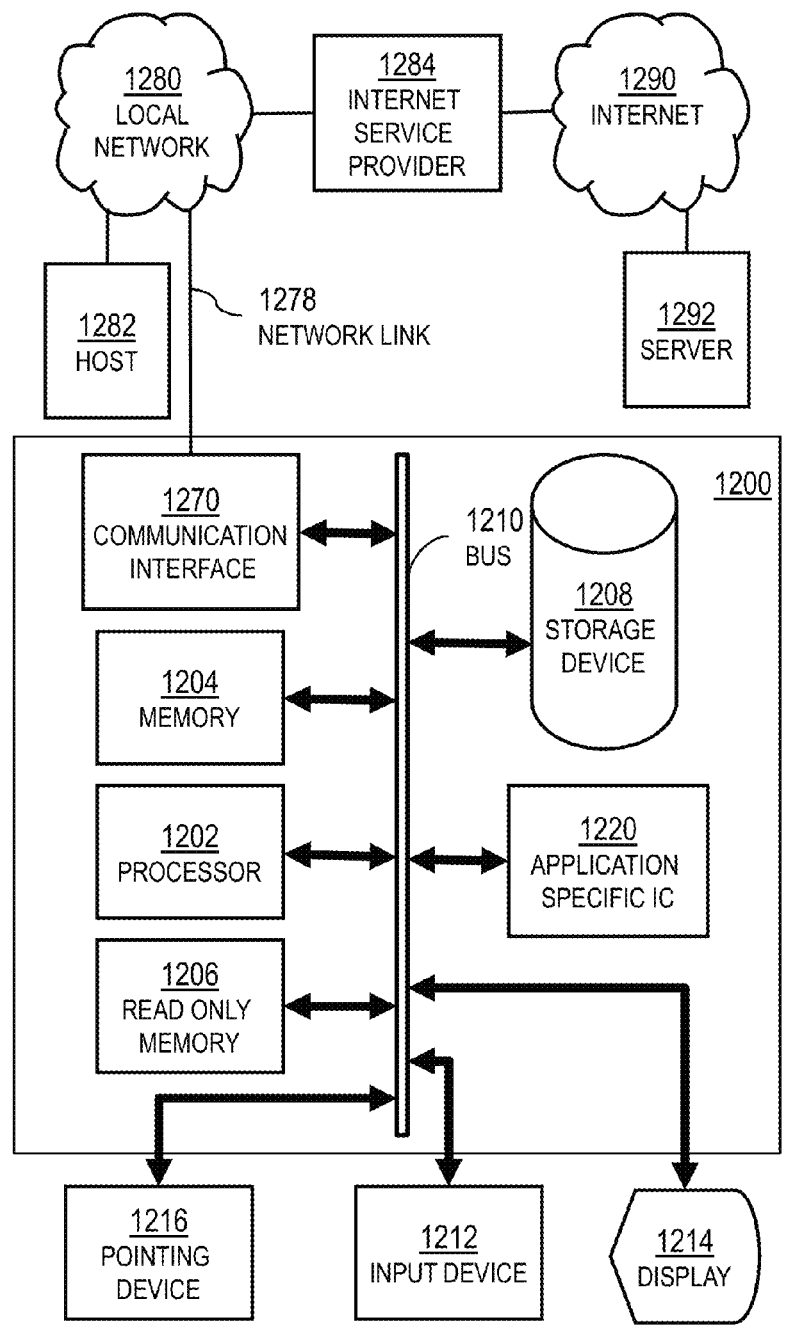
FIG. 12 is a diagram of computer hardware that can be used to implement an embodiment of the invention.

FIG. 12 illustrates a computer system 1200 upon which an embodiment of the invention may be implemented. Although computer system 1200 is depicted with respect to a particular device or equipment, it is contemplated that other devices or equipment (e.g., network elements, servers, etc.) within FIG. 12 can deploy the illustrated hardware and components of system 1200. Computer system 1200 is programmed (e.g., via computer program code or instructions) to perform one or more steps or portions thereof as described herein and includes a communication mechanism such as a bus 1210 for passing information between other internal and external components of the computer system 1200. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1200, or a portion thereof, constitutes a means for performing perform one or more steps or portions thereof.

A bus 1210 includes one or more parallel conductors of information so that information is transferred quickly among devices coupled to the bus 1210. One or more processors 1202 for processing information are coupled with the bus 1210.

A processor 1202 performs a set of operations on information as specified by computer program code. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 1210 and placing information on the bus 1210. The set of operations also typically include comparing two or more units of information, shifting positions of units of information, and combining two or more units of information, such as by addition or multiplication or logical operations like OR, exclusive OR(XOR), and AND. Each operation of the set of operations that can be performed by the processor is represented to the processor by information called instructions, such as an operation code of one or more digits. A sequence of operations to be executed by the processor 1202, such as a sequence of operation codes, constitute processor instructions, also called computer system instructions or, simply, computer instructions. Processors may be implemented as mechanical, electrical, magnetic, optical, chemical or quantum components, among others, alone or in combination.

Computer system 1200 also includes a memory 1204 coupled to bus 1210. The memory 1204, such as a random access memory (RAM) or other dynamic storage device, stores information including processor instructions. Dynamic memory allows information stored therein to be changed by the computer system 1200. RAM allows a unit of information stored at a location called a memory address to be stored and retrieved independently of information at neighboring addresses. The memory 1204 is also used by the processor 1202 to store temporary values during execution of processor instructions. The computer system 1200 also includes a read only memory (ROM) 1206 or other static storage device coupled to the bus 1210 for storing static information, including instructions, that is not changed by the computer system 1200. Some memory is composed of volatile storage that loses the information stored thereon when power is lost. Also coupled to bus 1210 is a non-volatile (persistent) storage device 1208, such as a magnetic disk, optical disk or flash card, for storing information, including instructions, that persists even when the computer system 1200 is turned off or otherwise loses power.

Information, including instructions, is provided to the bus 1210 for use by the processor from an external input device 1212, such as a keyboard containing alphanumeric keys operated by a human user, or a sensor. A sensor detects conditions in its vicinity and transforms those detections into physical expression compatible with the measurable phenomenon used to represent information in computer system 1200. Other external devices coupled to bus 1210, used primarily for interacting with humans, include a display device 1214, such as a cathode ray tube (CRT) or a liquid crystal display (LCD), or plasma screen or printer for presenting text or images, and a pointing device 1216, such as a mouse or a trackball or cursor direction keys, or motion sensor, for controlling a position of a small cursor image presented on the display 1214 and issuing commands associated with graphical elements presented on the display 1214. In some embodiments, for example, in embodiments in which the computer system 1200 performs all functions automatically without human input, one or more of external input device 1212, display device 1214 and pointing device 1216 is omitted.

In the illustrated embodiment, special purpose hardware, such as an application specific integrated circuit (ASIC) 1220, is coupled to bus 1210. The special purpose hardware is configured to perform operations not performed by processor 1202 quickly enough for special purposes. Examples of application specific ICs include graphics accelerator cards for generating images for display 1214, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1200 also includes one or more instances of a communications interface 1270 coupled to bus 1210. Communication interface 1270 provides a one-way or two-way communication coupling to a variety of external devices that operate with their own processors, such as printers, scanners and external disks. In general the coupling is with a network link 1278 that is connected to a local network 1280 to which a variety of external devices with their own processors are connected. For example, communication interface 1270 may be a parallel port or a serial port or a universal serial bus (USB) port on a personal computer. In some embodiments, communications interface 1270 is an integrated services digital network (ISDN) card or a digital subscriber line (DSL) card or a telephone modem that provides an information communication connection to a corresponding type of telephone line. In some embodiments, a communication interface 1270 is a cable modem that converts signals on bus 1210 into signals for a communication connection over a coaxial cable or into optical signals for a communication connection over a fiber optic cable. As another example, communications interface 1270 may be a local area network (LAN) card to provide a data communication connection to a compatible LAN, such as Ethernet. Wireless links may also be implemented. For wireless links, the communications interface 1270 sends or receives or both sends and receives electrical, acoustic or electromagnetic signals, including infrared and optical signals, that carry information streams, such as digital data. For example, in wireless handheld devices, such as mobile telephones like cell phones, the communications interface 1270 includes a radio band electromagnetic transmitter and receiver called a radio transceiver.

The term computer-readable medium is used herein to refer to any medium that participates in providing information to processor 1202, including instructions for execution. Such a medium may take many forms, including, but not limited to, non-volatile media, volatile media and transmission media. Non-volatile media include, for example, optical or magnetic disks, such as storage device 1208. Volatile media include, for example, dynamic memory 1204. Transmission media include, for example, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 1220.

Network link 1278 typically provides information communication using transmission media through one or more networks to other devices that use or process the information. For example, network link 1278 may provide a connection through local network 1280 to a host computer 1282 or to equipment 1284 operated by an Internet Service Provider (ISP). ISP equipment 1284 in turn provides data communication services through the public, world-wide packet-switching communication network of networks now commonly referred to as the Internet 1290.

A computer called a server host 1292 connected to the Internet hosts a process that provides a service in response to information received over the Internet. For example, server host 1292 hosts a process that provides information representing video data for presentation at display 1214. It is contemplated that the components of system 1200 can be deployed in various configurations within other computer systems, e.g., host 1282 and server 1292.

At least some embodiments of the invention are related to the use of computer system 1200 for implementing some or all of the techniques described herein. According to one embodiment of the invention, those techniques are performed by computer system 1200 in response to processor 1202 executing one or more sequences of one or more processor instructions contained in memory 1204. Such instructions, also called computer instructions, software and program code, may be read into memory 1204 from another computer-readable medium such as storage device 1208 or network link 1278. Execution of the sequences of instructions contained in memory 1204 causes processor 1202 to perform one or more of the method steps described herein. In alternative embodiments, hardware, such as ASIC 1220, may be used in place of or in combination with software to implement the invention. Thus, embodiments of the invention are not limited to any specific combination of hardware and software, unless otherwise explicitly stated herein.

The signals transmitted over network link 1278 and other networks through communications interface 1270, carry information to and from computer system 1200. Computer system 1200 can send and receive information, including program code, through the networks 1280, 1290 among others, through network link 1278 and communications interface 1270. In an example using the Internet 1290, a server host 1292 transmits program code for a particular application, requested by a message sent from computer 1200, through Internet 1290, ISP equipment 1284, local network 1280 and communications interface 1270. The received code may be executed by processor 1202 as it is received, or may be stored in memory 1204 or in storage device 1208 or other non-volatile storage for later execution, or both. In this manner, computer system 1200 may obtain application program code in the form of signals on a carrier wave.

Various forms of computer readable media may be involved in carrying one or more sequence of instructions or data or both to processor 1202 for execution. For example, instructions and data may initially be carried on a magnetic disk of a remote computer such as host 1282. The remote computer loads the instructions and data into its dynamic memory and sends the instructions and data over a telephone line using a modem. A modem local to the computer system 1200 receives the instructions and data on a telephone line and uses an infra-red transmitter to convert the instructions and data to a signal on an infra-red carrier wave serving as the network link 1278. An infrared detector serving as communications interface 1270 receives the instructions and data carried in the infrared signal and places information representing the instructions and data onto bus 1210. Bus 1210 carries the information to memory 1204 from which processor 1202 retrieves and executes the instructions using some of the data sent with the instructions. The instructions and data received in memory 1204 may optionally be stored on storage device 1208, either before or after execution by the processor 1202.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A particle of ring shape comprising:
   PEGDA of molecular weight about 700 daltons in an amount of at least 10 percent by volume;
   an active substance; and
   PEG of molecular weight about 200 daltons,
   wherein a total amount of PEG, PEGDA and active substance is from about 30 to about 95 percent by volume of the particle.

2. A particle as recited in claim 1, wherein the amount of PEGDA is selected to impart to the particle a stiffness in a range corresponding to a range of pressures to move an 8 micron particle through a constriction 4 microns across, wherein the range of pressures is between about 0.05 millimeters of mercury (mmHg) and about 100 mmHg.

3. A particle as recited in claim 1, wherein the active substance comprises a member of the group comprising drugs, detection labels including fluorophores, acrylic acid and other acrylate chemistries.

4. A particle as recited in claim 1, wherein the active substance comprises a biodegradable cross-linker molecule.

5. A particle as recited in claim 1, wherein the particle is bound to a target affinity molecule.

6. A ring shaped hydrogel particle having a diameter of about 3 microns and stiffness of a red blood cell comprising:
   PEGDA of molecular weight about 700 daltons in an amount of at least 10 percent by volume;
   an active substance; and
   PEG of molecular weight about 200 daltons.

7. A ring shaped hydrogel particle as recited in claim 6, wherein:
   a total amount of PEG, PEGDA and active substance is about 65 percent by volume of the particle.

8. A composition comprising a plurality of ring shaped particles, each particle comprising:
   PEGDA of molecular weight about 700 daltons in an amount of at least 10 percent by volume;
   an active substance; and
   PEG of molecular weight about 200 daltons,
   wherein a total amount of PEG, PEGDA and active substance is from about 30 to about 95 percent by volume of the particle.

9. A composition as recited in claim 8, wherein the composition is formulated for administration to an animal.

10. A composition as recited in claim 8, wherein the animal is a mammal and the particle is administered intravenously, intraarterially, intraperitoneally or in cerebrospinal fluid of the animal.

11. A composition as recited in claim 8, wherein the composition is formulated for topical administration to an animal.

12. A composition as recited in claim 8, wherein the composition is formulated as a paint additive.

13. A composition as recited in claim 8 wherein the composition is formulated for animal consumption.

14. A composition as recited in claim 9, wherein the particle is a ring shaped hydrogel particle having a diameter of about 8 microns and a stiffness of red blood cells.

* * * * *